US008916383B2

(12) United States Patent
Barreiro et al.

(10) Patent No.: US 8,916,383 B2
(45) Date of Patent: Dec. 23, 2014

(54) APPARATUS AND METHODS TO GAIN ACCESS TO AND EXTRACT INTACT IMMATURE EMBRYOS FROM DEVELOPING MAIZE KERNELS OR SPECIFIC INTERNAL TISSUE OR STRUCTURES FROM ONE OR MORE SEEDS

(75) Inventors: Roberto Barreiro, Kapolei, HI (US); Jason M. Cope, Ankeny, IA (US); Daniel M. Goldman, Des Moines, IA (US); James L. Hunter, Littleton, CO (US); Alessandro Pellegrineschi, Wilmington, DE (US)

(73) Assignee: Pioneer Hi Bred International Inc, Johnston, IA (US)

( * ) Notice: Subject to any disclaimer, the term of this patent is extended or adjusted under 35 U.S.C. 154(b) by 476 days.

(21) Appl. No.: 12/853,997

(22) Filed: Aug. 10, 2010

(65) Prior Publication Data

US 2011/0054969 A1    Mar. 3, 2011

Related U.S. Application Data

(60) Provisional application No. 61/233,309, filed on Aug. 12, 2009.

(51) Int. Cl.
*C12N 5/00* (2006.01)
*C12N 5/02* (2006.01)
*A01H 1/04* (2006.01)
*A01H 4/00* (2006.01)
*G06Q 10/06* (2012.01)

(52) U.S. Cl.
CPC .................. *A01H 4/001* (2013.01); *A01H 1/04* (2013.01); *A01H 4/003* (2013.01); *G06Q 10/0637* (2013.01)
USPC ........................................................ 435/420

(58) Field of Classification Search
USPC ........................................................ 435/420
See application file for complete search history.

(56) References Cited

U.S. PATENT DOCUMENTS

| 5,639,951 A | 6/1997 | Bosemark et al. |
| 6,872,136 B1 * | 3/2005 | Bennett .......................... 460/51 |

(Continued)

FOREIGN PATENT DOCUMENTS

| WO | WO 2006/022958 | 3/2006 |
| WO | WO 2007/038075 A1 | 4/2007 |

(Continued)

OTHER PUBLICATIONS

Green, C. E. et al., *Plant Regeneration from Tissue Cultures of Maize*, Crop Science, vol. 15, May-Jun. 1975, pp. 417-421.

(Continued)

*Primary Examiner* — Wendy C Haas
(74) *Attorney, Agent, or Firm* — Pioneer Hi-Bred Int'l Inc.

(57) ABSTRACT

A high throughput apparatus and method for gaining access to and extracting internal tissue or structure of interest from a seed or plurality of seed is disclosed. In one aspect, an apparatus utilizes means to expose the internal tissue or structure and means to separate at least some of the exposed internal tissue or structure for collection and evaluation. In one aspect, a method utilizes some force or action to expose the internal tissue or structure and some force or action to separate the internal tissue or structure.

11 Claims, 23 Drawing Sheets

(56) References Cited

U.S. PATENT DOCUMENTS

| | | |
|---|---|---|
| 7,150,993 B2 | 12/2006 | Davis et al. |
| 7,560,611 B2 | 7/2009 | Adams et al. |
| 7,658,033 B2 | 2/2010 | Martinell et al. |
| 7,735,626 B2 * | 6/2010 | Cope et al. ............... 198/381 |
| 7,915,006 B2 * | 3/2011 | Cope et al. ............... 435/40 |
| 7,968,282 B2 * | 6/2011 | Cope ............................ 435/4 |
| 8,286,387 B2 * | 10/2012 | Becker et al. ............ 47/58.1 SE |
| 8,313,053 B2 * | 11/2012 | Cope et al. ............... 241/270 |
| 8,519,297 B2 * | 8/2013 | Cope ........................... 219/121.6 |
| 8,535,877 B2 * | 9/2013 | Cope ............................ 435/4 |
| 8,579,118 B2 * | 11/2013 | Cope et al. ............... 209/607 |
| 2005/0032224 A1 | 2/2005 | Davis et al. |
| 2005/0246786 A1 | 11/2005 | Adams et al. |
| 2005/0254053 A1 | 11/2005 | Wright |
| 2009/0142837 A1 | 6/2009 | Adams, Jr. et al. |
| 2010/0044356 A1 | 2/2010 | Cope |
| 2010/0050300 A1 | 2/2010 | Cope |
| 2011/0078819 A1 | 3/2011 | Bullock |

FOREIGN PATENT DOCUMENTS

| | | |
|---|---|---|
| WO | WO 2008/061095 A2 | 5/2008 |
| WO | WO 2009/029852 | 3/2009 |
| WO | WO 2009/142752 | 11/2009 |

OTHER PUBLICATIONS

Partial International Search Report for Application No. PCT/US2010/045243 dated Nov. 9, 2010.

International Search Report and Written Opinion for International Application No. PCT/US2010/045243, mailed Dec. 13, 2010.

Fong, F., et al.; "Rapid isolation and purification of immature zygotic embryos"; [Online]; [Retrieved on Jan. 12, 2011]; Retrieved from the Internet <URL: http://www.agron.missouri.edu/mnl/59/42fong.html>; 3 pages.

* cited by examiner

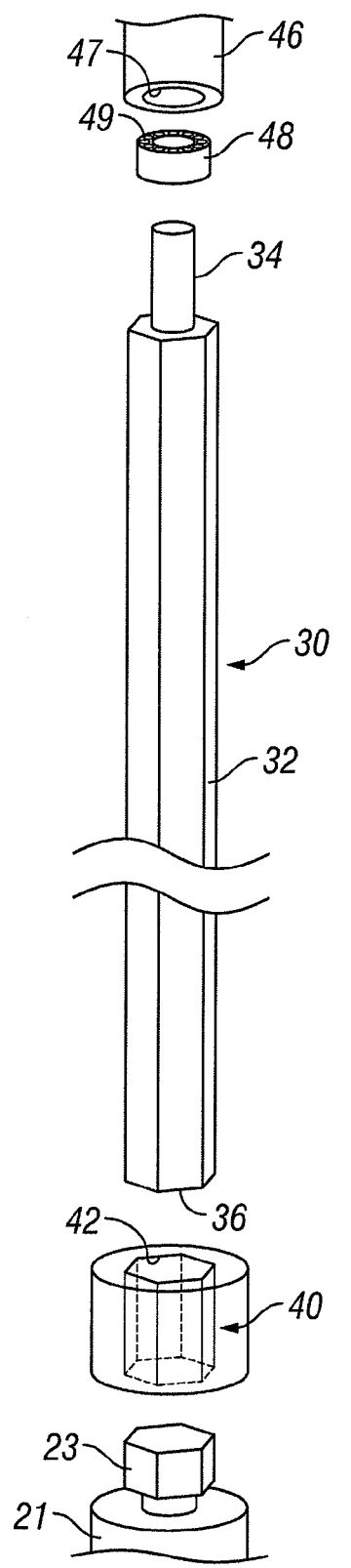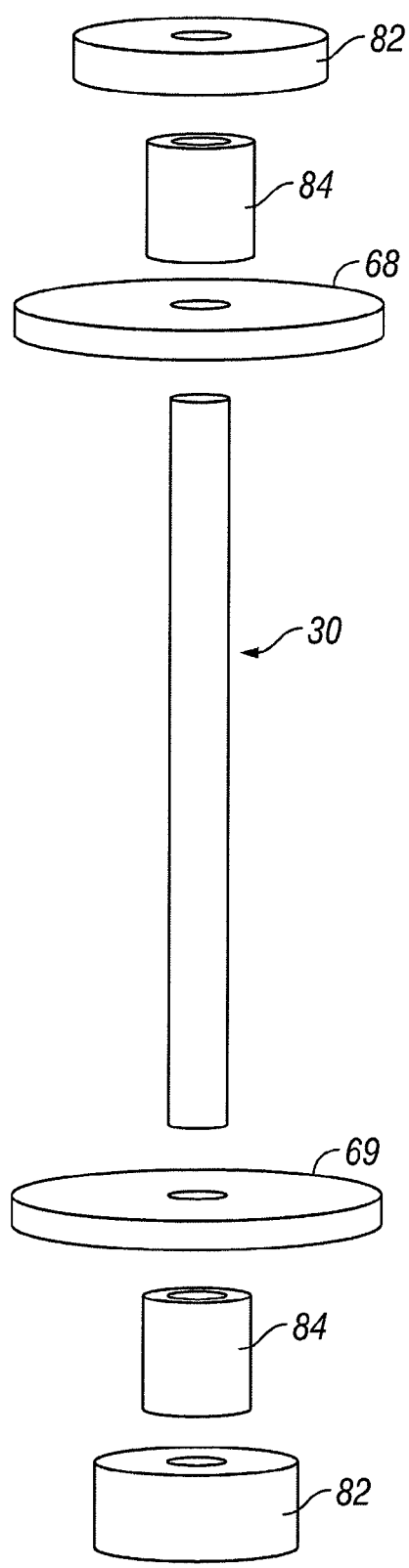
*FIG. 9A*  *FIG. 9B*

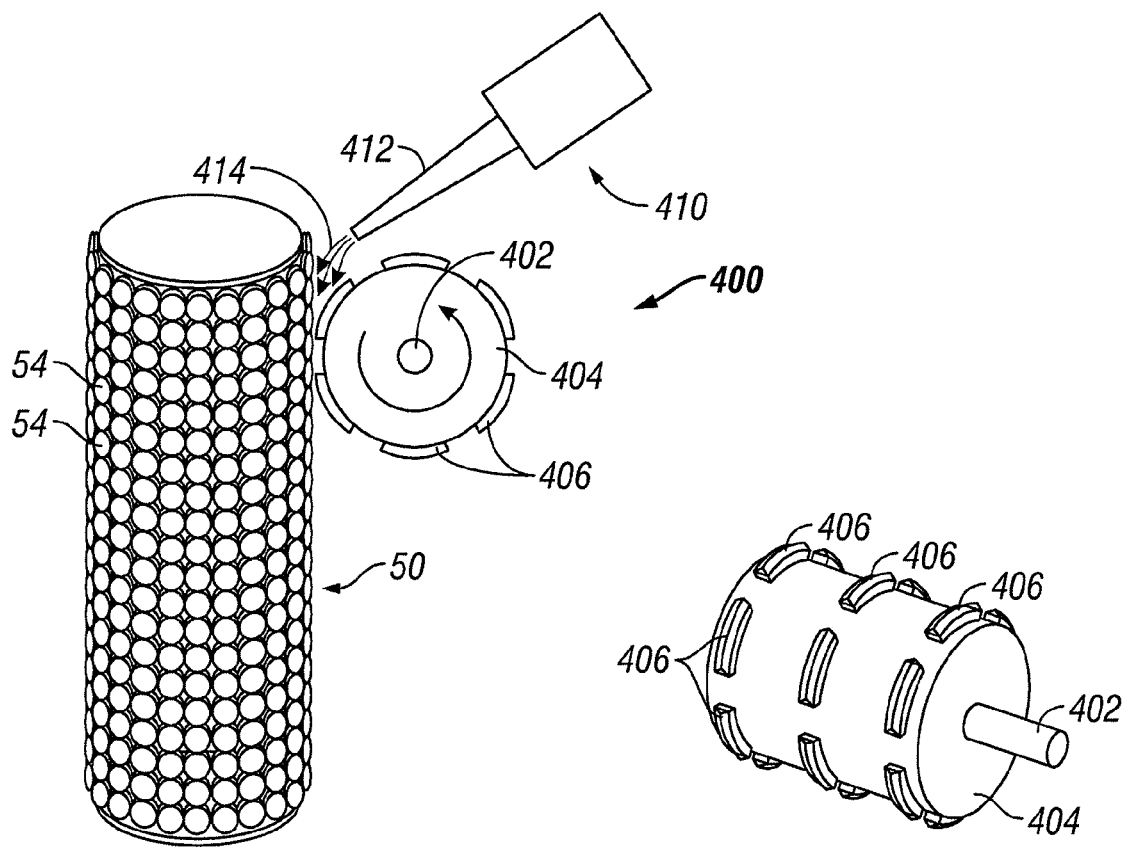
FIG. 20A  FIG. 20B
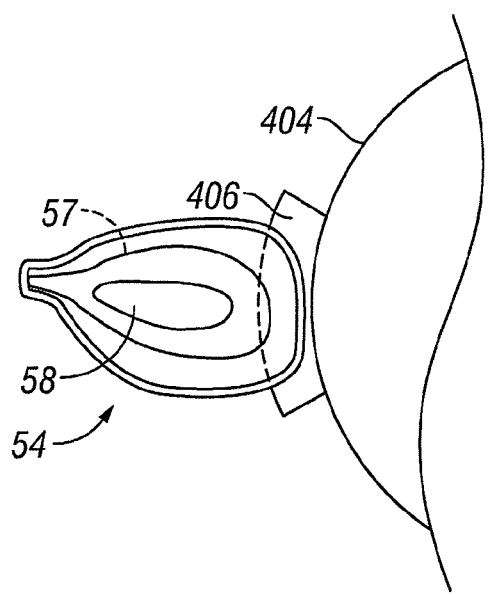
FIG. 20C

APPARATUS AND METHODS TO GAIN ACCESS TO AND EXTRACT INTACT IMMATURE EMBRYOS FROM DEVELOPING MAIZE KERNELS OR SPECIFIC INTERNAL TISSUE OR STRUCTURES FROM ONE OR MORE SEEDS

CROSS-REFERENCE TO RELATED APPLICATIONS

The present application claims priority from U.S. Provisional Application No. 61/233,309, filed Aug. 12, 2009, which is hereby incorporated herein by reference in its entirety.

BACKGROUND

1. Field of the Invention

The present invention relates to gaining access to and extracting specific internal tissue or structure of seed, and in particular, to a more efficient method or system of doing so in a relatively high throughput manner. The invention also relates to collecting extracted tissue or structure, including for evaluation by chemical, physical, or genetic testing, and in one aspect high throughput extraction of embryos suitable for enabling doubled haploid plant reproduction. One example of internal tissue or structure is the embryo of a maize seed.

2. State of the Art

The nature of most seeds makes access to and/or extraction of relevant tissue or structure non-trivial. While this can be done, seed-by-seed, in a labor-intensive, manual way (e.g. using a knife and tweezers), there is a need for a method of doing so in a more time and resource efficient manner.

For example, one of the most labor intensive steps in the process of doubled haploid plant production, such as with maize, is the extraction of immature embryos from the developing kernels. For maize kernels the term "immature" is used to mean less than physiological maturity, which normally means less than approximately 30 days or so after pollination or prior to total solidification of the endosperm or after black layer formation.

Extraction of embryos is done by hand at present, often under sterile conditions, which is tedious and time-consuming. In the case of maize, the most relevant genetic material is in the embryo of the seed. The embryo is encased by the endosperm. The endosperm, in turn, is encased in the pericarp, a relatively robust tissue. Additionally, maize kernels are relatively small in size, with the embryo being even smaller. Furthermore, the maize embryos and kernels develop biologically and temporally on a cob into an ear of corn, with a single ear generally having anywhere from a few to a few hundred kernels depending on genotype and growth conditions during plant and ear development. This increases the difficulty of extracting intact embryos. This also increases the complexity and difficulty of trying to automate, at least partially, the steps for accessing and then extracting an intact viable embryo, or a part of its tissue without destroying it or making it difficult to obtain accurate information from, or so that it is suitable for doubled haploid plant production.

There is also other internal tissue or structure in maize seed that may be of interest for efficient extraction. There are also other seed types and species which have at least some of the same or similar issues to maize and which have internal tissues or structures that could be of interest to access by non-destructive extraction.

Manual embryo extraction, especially on a seed-by-seed or kernel-by-kernel basis, is not a high throughput process. In commercial product development operations, time can be of the essence. Hundreds, if not thousands, of seed samples may need to have embryo tissue extracted in a relatively short time. With a manual process, substantial labor resources must be allocated to the task in order to achieve extraction of large numbers of embryos or other seed tissues in this short time frame, for subsequent analysis or use. Consider the example of a substantial size maize seed company. It may handle hundreds of thousands, and more often millions, of seeds per year. Depending on the age, attained growth and stage of development of the embryos, it is possible that present state of the art manual extraction methods could result in embryo extraction rates as low as 600 embryos per worker per hour, and in the best case scenario as much as 800 embryos per worker per hour. At this rate, as an example, processing 1 million seed would take well over a thousand worker hours. Moreover, embryo extraction rates using manual extraction techniques can vary as much as 300-400 embryos per worker per hour depending on the stage of development of the embryos (i.e., the number of days that have elapsed since pollination).

In commercial maize seed research and plant production, knowledge of a seed's phenotype and genotype saves time and effort by avoiding the need to grow plants from the seed and subsequently test plant tissue to look for desirable heritable traits or characteristics, thereby justifying its use in subsequent research and/or commercialization. Notwithstanding this effort, growing experimental plots of plants from seed for selection for commercial quantities is widely practiced in the maize seed business. Eliminating time and resources needed for this step is beneficial in a number of ways. Both time and significant resources in terms of labor and processing (e.g. planting, tilling, maintenance, obtaining tissue samples, etc.) would be saved. Moreover, the need for substantial amounts of land for growing the requisite plots could be greatly reduced. Decisions about a plant could be made when seed is developing or yet immature, as opposed to waiting for one or more subsequent generations to be grown. Additionally, efficient extraction of viable embryos could be used to harvest embryos for further use such as in the reproduction of succeeding generations of plants, and is particularly suitable for use in the process of doubled haploid plant production. This would facilitate shorter time to market, use of less space, time and resources, and the harvest of more embryos, more quickly.

Similar issues to those set forth above exist for other plants and seeds. It is beneficial to be able to obtain reliable information about a seed to make decisions about that plant without having to grow a subsequent generation and test tissue from the plant to make such decisions. It is also beneficial to extract, in a relatively high throughput manner, internal tissue(s) or structure(s) of the seed. It is therefore beneficial to quickly and efficiently extract internal tissue or structure from maize or other species.

Thus, a need exits for a more efficient way of harvesting or extracting embryos or embryo tissue from maize kernels for use in doubled haploid plant production. In this context, "efficiency" means a higher throughput of extracting embryos or tissues from multiple kernels in a given time period. Efficiency can also mean extraction of the embryo tissue without destroying it (i.e., extraction of intact viable embryos) or requiring substantial post-extraction steps to isolate the embryo tissue. Analogous issues and needs exist with other internal tissue or structure of maize and with internal tissue or structure of other types of seed plants. Benefits from an efficient and accurate method of accessing and extracting relevant internal seed tissue or structure exist for other such seed, as well as maize seed.

BRIEF SUMMARY OF VARIOUS EMBODIMENTS

In a method according to one aspect of the invention, external tissue or structure is removed from one or more seed to gain access to specific internal seed tissue or structure. Alternatively, the external tissue is damaged, weakened to create a point of failure or fracture, or otherwise disrupted such that the specific internal seed tissue or structure can be accessed, released or removed for testing or for other use. The specific targeted internal tissue or structure is extracted, removed or separated in at least a semi-automated fashion. The method can enable the simultaneous or concurrent extraction of multiple individual intact embryos or other internal tissues from multiple individual seeds.

The removed or separated internal tissue or structure can be isolated to remove or deter any contamination (e.g. for genetic testing). Results of testing can be used to make decisions about the seed and its plant. In one aspect, decisions can be made whether the seed and its plant have inheritable traits or characteristics that are deemed desirable to make commercial quantities of the seed. Other uses of viable embryos, for example, could include use of the embryo for making doubled haploid plants.

In one aspect of the above-described method, embryo tissue of multiple maize kernels is made accessible while the seed is attached to its cob. The embryo tissue is then extracted and isolated from the ear and other parts or tissue associated with the seed. The embryo tissue is then evaluated. The evaluation is used, for example, in determining if the kernel has a trait or characteristic that is desirable for further research and development or for commercialization. Another use for the extracted embryo is for evaluation and growing of one or more succeeding generations of plants, such as in the process of doubled haploid plant production. In one aspect, the method can be conducted for immature but viable maize embryos. A force is imparted upon the seed which facilitates access to or exposes the embryos. A force is then imparted upon the seed which extracts, releases or separates embryo tissue from the kernels. This allows mechanization or automation of at least a certain number of steps for enabling high throughput embryo extraction. In one aspect, the force to gain access to maize embryos within a kernel is a cutting force or action with a cutting blade, laser beam, or other tool to physically remove the crown of the kernels while on the ear. The force to extract the embryos includes (a) use of centripetal force to subject the kernels to centripetal acceleration by rotation of the ear around its longitudinal axis and (b) selection of the magnitude of centripetal acceleration to produce sufficient reactive or real centrifugal force to cause removal, disruption, or breaking of the centripetal force tending to hold the tissue or structure to the rotating ear to influence release of the internal tissue or structure, including the embryo, out of the cut-open kernels and in a manner that keeps it intact. With a properly applied force, each embryo and/or the internal tissue or structure of each kernel travels or 'flies' off of the ear in a generally straight line radially from the rotational axis of the rotating ear. The released materials can be collected for subsequent use.

An apparatus according to the present invention facilitates the above-described methods. In one aspect, the apparatus includes a motor operably connected to a receiver or holding devices. The motor is capable of generating rotation of the receiver or holder at speeds which can generate g forces on the kernels sufficient to release the embryo and sometimes other internal tissue and structure from the kernel. In one aspect, a container surrounds the ear and collects the embryos and other internal tissue or structures which separate from the rotating ear.

BRIEF DESCRIPTION OF THE DRAWINGS

FIG. 9A is an enlarged perspective view of a spindle on which the ear of FIG. 8 can be placed and rotated in the blender device of FIG. 2.

FIG. 9B illustrates an optional arrangement of additional rotational support of the spindle of the blender of FIG. 2.

FIG. 20A is a diagrammatic view of another embodiment according to the present invention using a fine puncture or slicing tool to open, damage or weaken the seed coat to prepare for extraction of internal tissue.

FIG. 20B is a perspective isolated view of a roller with puncturing or perforating tools used in the embodiment of FIG. 20A.

FIG. 20C is an enlarged illustration of puncturing of a kernel with the apparatus of FIG. 20A.

DETAILED DESCRIPTION

Overview

Figure 1:
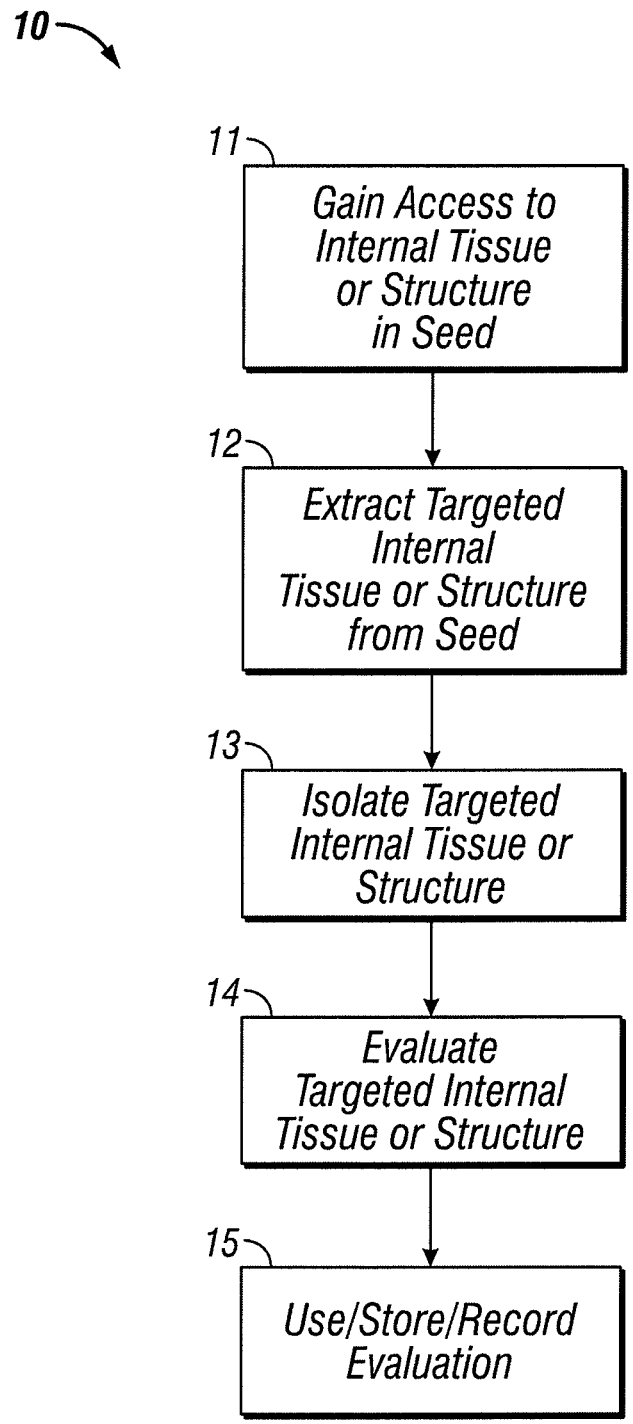
FIG. 1 is a flow chart of a general method according to one exemplary embodiment of the invention.

For a better understanding of the invention, several exemplary embodiments will now be described in detail. Reference will be made from time-to-time to the appended drawings. Reference numerals will be used to indicate certain parts or locations in the drawings. The same reference numerals will indicate the same parts or locations throughout the drawings unless otherwise indicated.

General Method

One aspect of the invention seeks a more efficient way to access and extract internal tissue from seed so that it can be evaluated and the evaluation used for any number of given purposes, including but not limited to, evaluation of the internal tissue for purposes of selection of genotypes or phenotypes for commercial production by a seed company, such as where extracted intact embryos are suitable for use in the process of doubled haploid plant production.

The phrase "suitable for use in the process of doubled haploid plant production" refers to the extraction of haploid immature embryos or doubled haploid embryos from developing maize kernels for high throughput production of doubled haploid plants, where the doubled haploid or doubled haploid plant or cell is one that is developed by the doubling of a haploid set of chromosomes.

A "haploid immature embryo" is defined generally as the embryo formed after one sperm nucleus from a pollen grain fuses with the polar nuclei in the embryo sac to create a triploid (3N) endosperm.

A "doubled haploid embryo" is generally understood to be an embryo that has one or more cells that contain two sets of homozygous chromosomes. For example, methods of the present invention may be used to extract targeted plant tissue, such as a maize embryo where chromosomes have been doubled at the immature embryo stage, at the mature seed stage, or any time between pollination of the plant and before the germination of the haploid seed.

Any one of the extraction methods of the present invention may be used to extract and isolate immature haploid embryos that are to undergo chromosomal doubling. The haploid embryos to be isolated may be in the seed or kernel, may be in the kernel on a slice of the cob, may be on the ear, or may be in the kernel which is on the ear and on the plant.

The present invention provides apparatus and methods for extraction and isolation of immature haploid embryos suitable for use in the process of doubled haploid plant production. For example, kernels, and specifically the cap of the kernel may be removed, and sliced, roughened, weakened, thinned, punctured, or otherwise altered to weaken or predispose the kernel to open upon sufficient application of force to allow for extraction of intact, immature embryos for use in the process of doubled haploid production, such as for example, where the extracted embryos are contacted by a doubling agent for producing a doubled haploid embryo.

Another aspect of the present invention provides extraction and isolation of doubled haploid maize embryos suitable for use in the process of doubled haploid plant production. For example, doubled haploid embryos may be developed while the ear is on the plant by contacting the plant with a doubling agent. The doubled haploid embryos may be extracted and isolated using one or more of the apparatuses and methods of the present invention.

Suitable procedures for doubled haploid plant production are well known in the art. See, for example, methods for obtaining haploid plants disclosed in Kobayashi, M. et al., J. of Heredity 71(1):9-14, 1980, Pollacsek, M., Agronomie (Paris) 12(3):247-251, 1992; Cho-Un-Haing et al., J. of Plant Biol., 1996, 39(3):185-188; Verdoodt, L., et al., February 1998, 96(2):294-300; Genetic Manipulation in Plant Breeding, Proceedings International Symposium organized by EUCARPIA, Sep. 8-13, 1985, Berlin, Germany; Chalyk et al., 1994, Maize Genet Coop. Newsletter 68:47; Chalyk, S. T., 1999, Maize Genet. Coop. Newsletter 73:53-54; Coe, R. H., 1959, Am. Nat. 93:381-382; Deimling, S. et al., 1997, Vortr. Pflanzenzuchtg 38:203-204; Kato, A., 1999, J. Hered. 90:276-280; Lashermes, P. et al., 1988, Theor. Appl. Genet. 76:570-572 and 76:405-410; Tyrnov, V. S. et al., 1984, Dokl. Akad. Nauk. SSSR 276:735-738; Zabirova, E. R. et al., 1996, Kukuruza I Sorgo N4, 17-19; Aman, M. A., 1978, Indian J. Genet Plant Breed 38:452-457; Chalyk S. T., 1994, Euphytica 79:13-18; Chase, S. S., 1952, Agron. J. 44:263-267; Coe, E. H., 1959, Am. Nat. 93:381-382; Coe, E. H., and Sarkar, K. R., 1964 J. Hered. 55:231-233; Greenblatt, I. M. and Bock, M., 1967, J. Hered. 58:9-13; Kato, A., 1990, Maize Genet. Coop. Newsletter 65:109-110; Kato, A., 1997, Sex. Plant Reprod. 10:96-100; Nanda, D. K. and Chase, S. S., 1966, Crop Sci. 6:213-215; Sarkar, K. R. and Coe, E. H., 1966, Genetics 54:453-464; Sarkar, K. R. and Coe, E. H., 1971, Crop Sci. 11:543-544; Sarkar, K. R. and Sachan J. K. S., 1972, Indian J. Agric. Sci. 42:781-786; Kermicle J. L., 1969, Mehta Yeshwant, M. R., Genetics and Molecular Biology, September 2000, 23(3):617-622; Tahir, M. S. et al. Pakistan Journal of Scientific and Industrial Research, August 2000, 43(4):258-261; Knox, R. E. et al. Plant Breeding, August 2000, 119(4): 289-298; and U.S. Pat. No. 5,639,951 the disclosures of which are incorporated herein by reference.

At a high level, FIG. 1 illustrates basic steps of a general exemplary method 10 of the present invention.

Gain Access to Internal Tissue or Structure

Access to the internal structure in a seed is gained by some force or energy imparted on, to, or in the seed (step 11). The force or energy can be any of a number of possibilities that results in at least exposure of internal seed tissue or structure, or weakening or creating a point of failure in or to the external seed structure.

One example is cutting force or action to remove external tissue and structure to expose relevant internal tissue or structure. The cutting force or action can be by any of a number of methods and apparatuses.

Other forces or ways to gain internal access by exposing or creating an opening to the seed interior are possible. Non-limiting examples include abrasion or grinding, scarifying, fracturing, slicing, eroding, puncturing, and laser ablation or etching of the exterior tissue or structure of the seed (e.g. the seed coat or pericarp).

Alternatively, instead of removing or opening external seed structure or tissue, some type of weakening of the external tissue or structure, such as the seed coat, can prepare the seed for extracting targeted internal tissue or structure. By "targeted" it is meant that sometimes specific internal tissue or structure (as opposed to all internal tissue or structure) is desired, but to get to it other internal tissue, structure, or material must be, or is inherently extracted, with it. An example with maize is the endosperm, which essentially encases the maize embryo. In some embodiments, at least some endosperm is removed with the embryo. Because of the structure of a maize seed, it can be more efficient to simply extract non-targeted tissue or structure together with the desired tissue than try to first remove the endosperm, or try to just remove the embryo. The embryo is then separated or isolated from the endosperm (or other non-embryo material), and in one aspect of the present invention used in the process of doubled haploid plant production.

The weakening of the seed exterior could result in the creation of a point of failure. The weakening could be manifested in disruption of the external seed tissue or structure to make it easier to access and extract the internal tissue or structure. Non-limiting examples include some of the same as mentioned above regarding removing or exposing. The difference is the force(s) used to weaken, damage, disrupt, or make the external tissue or structure (e.g. the container or surrounding structure of the interior) more conducive to subsequent extraction of interior materials. One example is use of osmotic pressure. Another is to grind the seed coat to weaken but not remove it or completely penetrate it.

Other considerations for embryo extraction include manipulation or preparation of the internal tissue of each kernel to promote embryo extraction and lessen the force requirement needed to separate the embryo from any internal tissue, such as the endosperm. One method for manipulating or preparing the internal tissue to promote easier embryo extraction includes applying a pressure or force to the kernels sufficient enough to soften or weaken solidified endosperm within the kernel. Such pressure or force should be sufficient enough to soften or weaken the endosperm to prevent the endosperm from blocking extraction of the embryo. In one aspect of the present invention, pressure or force is applied to the kernels for softening or weakening the internal tissue (i.e., the endosperm) by rolling the ear of corn on a hard, or flat surface with sufficient pressure so as to soften or weaken the endosperm but without rupturing or bursting the pericarp. Other means for applying pressure or force to the kernels while on the ear are contemplated herein. For example, automated rollers, whether flat surfaced or curved could be actuated up and down or around the ear of corn to apply pressure to the kernels, but without rupturing the kernels. The methods of the present invention have experienced measurable improvement in embryo extraction and number of intact embryos extracted as a result of softening or weakening the endosperm before extraction. For example, in the case of centrifugal embryo extraction, rolling the ear of corn reduces the revolutions per minute (rpm) needed for embryo extraction, increases the embryo extraction rate and increases the number of intact embryos extracted.

In one aspect of the present invention, by rolling the ear of corn prior to removal of the cap of kernels, a reduction of nearly 3000 rpm (from 12,000-9,000) was attained in the rpm needed to extract embryos. Rolling the ears or otherwise softening or weakening the internal tissue to which the embryo adheres to resulted in an 80-90% embryo extraction rate with the embryos being intact and this was achieved at a reduced rpm. When a higher rpm was used but no measures were taken to soften or weaken the endosperm, a higher proportion of the embryos are damaged by the extraction process (e.g., rpm>12,000) and the embryo extraction rate was lower.

Many times it is desirable that the force or energy be controllable to remove external tissue or structure non-destructively, or to remove the targeted internal tissue or structure. For example, it can be desirable to gain access to and extract all or part of an embryo of a maize seed and grow a plant or plantlet from it, or use the embryo or cells for the specific purpose of producing doubled haploid parts. In a broad sense, the term non-destructive can mean non-impairing to the internal tissue or structure of interest. Germination potential means viability, namely to maintain the ability of the embryo or cells from it to give rise to cells, a plantlet or plant.

In summary, access is intended to describe different ways to manipulate or affect external seed tissue or structure to enable high throughput removal of internal tissue or structure, including targeted internal tissue or structure. As described, some of the methods of access include removal of external tissue (e.g. at least a portion of the seed coat), creating damage or a point of failure in the external tissue or structure, or bursting or weakening the external tissue from inside the seed (e.g. osmotic pressure or squeezing).

Some of the forces that can be used include, but are not limited to, mechanical tools (e.g. for cutting, slicing, grinding, puncturing, etc.); laser beams (for cutting, etching, ablating, etc.); or water pressure (osmotic pressure). Mechanical force (e.g. squeezing) can be used to press the seed to burst the seed coat.

Extract Targeted Internal Tissue or Structure

After access to, or weakening or disruption of the outer tissue or structure of the seed, the method extracts targeted or relevant internal tissue or structure (step 12). Extraction can be of just the targeted internal tissue or structure, or can be with other internal structure or tissue. In the example of maize seed, with the embryo being the targeted internal tissue, once the external tissue or structure (seed coat) is manipulated to gain access to the interior of the seed, the embryo as well as other internal tissue or structure (e.g., endosperm) can be extracted. The embryo can then be separated or isolated according to any of a number of methods.

Extraction is intended to mean the disruption of the internal structure of the seed to facilitate separation of the targeted internal structure from other non-targeted internal tissue or structure and from an enclosing or containing structure or seed coat.

In one aspect, the separation is by some force or energy other than manual. Non-limiting examples include ejection of the targeted internal tissue or structure by reactive or real centrifugal force, mechanized tools, air or water pressure, or vacuum. Another example is use of osmotic pressure to force the internal contents out. Another is use of tools to peel away or force the seed coat off the internal contents.

As can be appreciated, some of the methods and apparatus to extract internal tissue or structure could be the same as used to access internal tissue or structure. For example, some methods to disrupt or weaken the seed coat could also facilitate or influence separation of the targeted internal tissue or structure from the seed coat. An example is osmotic pressure. Another example is a brush, which could erode the seed coat and then subsequently be used to sweep the internal contents out.

The forces or actions of extracting internal seed tissue or structure can differ from those used to disrupt the seed coat or external tissue or structure to access the internal tissue or structure. One example is to use cutting action to remove a part of the seed coat and then centripetal acceleration to influence release of the internal contents. Another is laser ablation to remove or weaken the seed coat and then use vacuum or water pressure to influence release of the internal contents. Other combinations are, of course, possible.

Isolate the Targeted Internal Tissue or Structure

The extracted targeted internal tissue or structure (e.g., maize embryo) is then isolated from the remainder of the kernel or non-kernel material (step 13). In one aspect, this separation or isolation occurs automatically in the separation step 12. By isolation it is meant that the targeted internal material is separated from other material (e.g., other internal tissue or structure, pieces of external tissue or structure, or non-seed debris) or purified. Essentially, any irrelevant or contaminating material (non-embryo material) is separated from the embryos. This can be done in a number of ways. This allows testing, such as genetic testing, to be accurate.

The isolated targeted internal tissue or structure of step 13 is then evaluated (step 14). This can be by any type of evaluation appropriate or desired for a given application. A few non-limiting examples for seed are physical evaluation, chemical evaluation, and/or genetic evaluation. In the example of maize embryos, by known genetic evaluation methodologies, genetic information related to an embryo can be obtained and used in, for example, seed company selection processes for selecting markers, plants or genotypes for further research and development or commercial production, such as in the case of doubled haploid plant production. As will be understood by the skilled artisan, uses of the evaluation of the targeted internal tissue or structure (step 15) can cover a wide range and variety.

Method 10 of FIG. 1 provides a process by which at least some steps can be mechanized or automated. Additionally, the method can be applied to multiple seed or kernels, including multiple seed or kernels still attached to their vegetative carrier (e.g., the cob for maize). This lends itself to at least semi-automation and higher throughput for more efficient access to and extraction of internal seed tissue, such as maize embryos for example. Analogous uses and advantages exist for other internal tissues or structures of maize seed (one example being endosperm). Some non-limiting examples of classes of plants which can be used in the methods of the present invention include monocotyledonous and dicotyledonous plants. Method 10 might be applied where there is a need to liberate or collect some internal tissue or structure from the outer protective packet or coat of a seed.

The targeted internal tissue or structure can be isolated and evaluated, and the evaluation used, stored, or recorded.

The method of FIG. 1 therefore promotes the following:

Higher throughput extraction of targeted internal tissue or structure from seed. In the case of maize, embryos can be highly valuable. It lends itself to at least partial automation or mechanization.

Non-destructive extraction of targeted internal tissue or structure. In the case of maize, the method can be adapted to extract embryos in a way that is non-impairing to the embryos or at least some of their cells.

Efficient extraction. In the case of maize, embryos or other internal tissue or structure can be extracted from multiple seed with a high rate of recovery. In other words, the method promotes a relatively high and useful ratio of extracted targeted internal tissue or structure relative to total seed processed.

Low contamination risk. The method promotes low risk of cross-contamination with other sample sets of seed or contamination from non-seed materials.

In at least one aspect, high throughput extraction of embryos suitable for use in doubled haploid plant production.

The following Exemplary Embodiments 1 through 9 therefore promotes at least the following relative to the harvesting embryos from an ear of maize:

harvesting a high proportion of embryos efficiently, harvesting embryos non-destructively, harvesting embryos quickly, many times in less than one minute, harvesting embryos with low contamination risk, harvesting embryos in at least a partially automated fashion, and in at least one aspect, promoting high throughput extraction of embryos suitable for use in doubled haploid plant production.

Exemplary Embodiment 1

FIGS. 2-13 illustrate a first specific exemplary embodiment apparatus 20. An ear of maize 50 is pre-processed to cut off crowns 54A of each kernel 54 on a cob 53 in a manner which exposes internal tissue or structure (principally endosperm 56) of each kernel 54 (see FIG. 5-8). As described earlier, in immature maize kernels, endosperm 56 is generally not solidified (almost liquid like) and substantially surrounds embryo 58. The processed ear 50 is mounted on a driven spindle 30 positioned vertically in a commercial blender container 26, in turn operably mounted in a blender 20. The spindle 30 is rotated at a relatively high rpm, which rotates ear 50 in kind. The blender container lid 28 is secured to container 26. The rotational speed is selected to generate reactive or real centrifugal forces sufficient to influence separation of at least some interior endosperm 56 and embryo 58 from the remaining portion of the kernels 54B with crowns 54A removed. The ejected endosperm 56/embryo 58 materials from the kernels are contained and collected in the blender container 26. The rpm of blender 20 is selected so that most, if not all, other parts of the kernels 54 remain attached to cob 53 and ear 50 remains attached to spindle 30. Embryos 58 within container 26 are then available for isolation and evaluation.

Stated another way, the endosperm and embryo are made accessible by cutting or shaving the kernel tops or crowns while on the ear, and spinning the ear about its longitudinal axis to use reactive or real centrifugal force to separate the embryos from the kernels. This is useful for high throughput extraction of maize immature embryos (sometimes up to approximately 32 days after pollination). At that stage of maize development, the stem apical meristem should appear terminal and the silk scar is still evident on the distal portion of the kernel. The anatomical isolation of the maize embryo allows for ready detachment through the mostly liquid endosperm. Vectorial acceleration extracts the embryo from the kernel. This process allows batch extraction of embryos. There are typically several hundred kernels per ear at this stage of maturation. Therefore, even if not all embryos separate, the method will generally produce many more than a few embryos, and more likely at least more than one hundred in a batch.

The method could also be used to extract immature embryos from seed of other plant species. It can also be used to extract or eject material from other seed where the centripetal acceleration influences the material out of (or separates it from) the external or encasing seed material (e.g. creates g forces that can cause removal of or overcome centripetal forces (e.g., tensile, adhesive, or other forces) holding internal tissue or structure to the seed), and thus results in separation from the seed.

In one form, apparatus 20 includes a blender base 22 including an electrical motor 21 with a drive shaft 23. Blender container 26 includes a closed bottom 24 that mates into base 22. A drive connection 40 complementarily mates with a gear on drive shaft 23. Driven spindle 30 has an outer geometry on its lower end 36 that mates into complementary geometry 42 of drive connection 40. Driven spindle 30, including its middle section 32, extends along a vertical axis generally centered in container 26 to a round cross sectional upper end 34.

Blender container lid 28 has an integrally formed sleeve 46 of a tubular shape having an open bottom end in which a roller or other bearing 48 is operatively positioned. When lid 28 is latched by clamping latches 29 to the open upper end of blender container 26, upper end 34 of driven shaft 30 extends into bearing 48 and is held between drive connection 40 and lid 28.

By this arrangement, rotation of drive shaft 23 of motor 21 of blender 20 rotates drive connection 40 in correspondence, which rotates driven spindle 30 in correspondence. The upper end 34 of driven spindle 30 would be supported within sleeve 47 and rotate within bearing 48 of fixed receiver 46. Fixed receiver 46 is separated from round cross sectional upper end 34 by ball bearings 49.

As described above and as illustrated in FIGS. 2, 3, and 5-8, maize ear 50 is pre-processed before it is positioned on spindle 30. Original ear 50 is husked to leave kernels 54 on cob 53 (see FIG. 5). A knife 60 having a sharp blade 62 is used to essentially cut off the crowns 54A of each kernel along cut line 64 (see FIG. 6) while the kernels 54 remain attached to the cob 53. By crown it is meant the distal portion of the cariopsis or the point farthest from point of attachment or origin.

Each kernel 54 has an outer pericarp layer 55. The embryo 58 is in a chamber 57 that is surrounded by endosperm 56. Cutting off the crown 54A of a kernel 54 at an appropriate distance (see for example cut line 7-7 in main FIG. 6 and its enlargement), results in exposing the endosperm inside the kernel (see FIG. 7). By making approximately this same cut for each kernel on the cob, and by cutting off the top and bottom of ear 50 (see cut lines 66 and 67 respectively in FIGS. 5 and 8), a relatively flat top and bottom ended section of the original ear, with kernels intact but interior exposed, is available for mounting in blender device 20.

Figure 5:
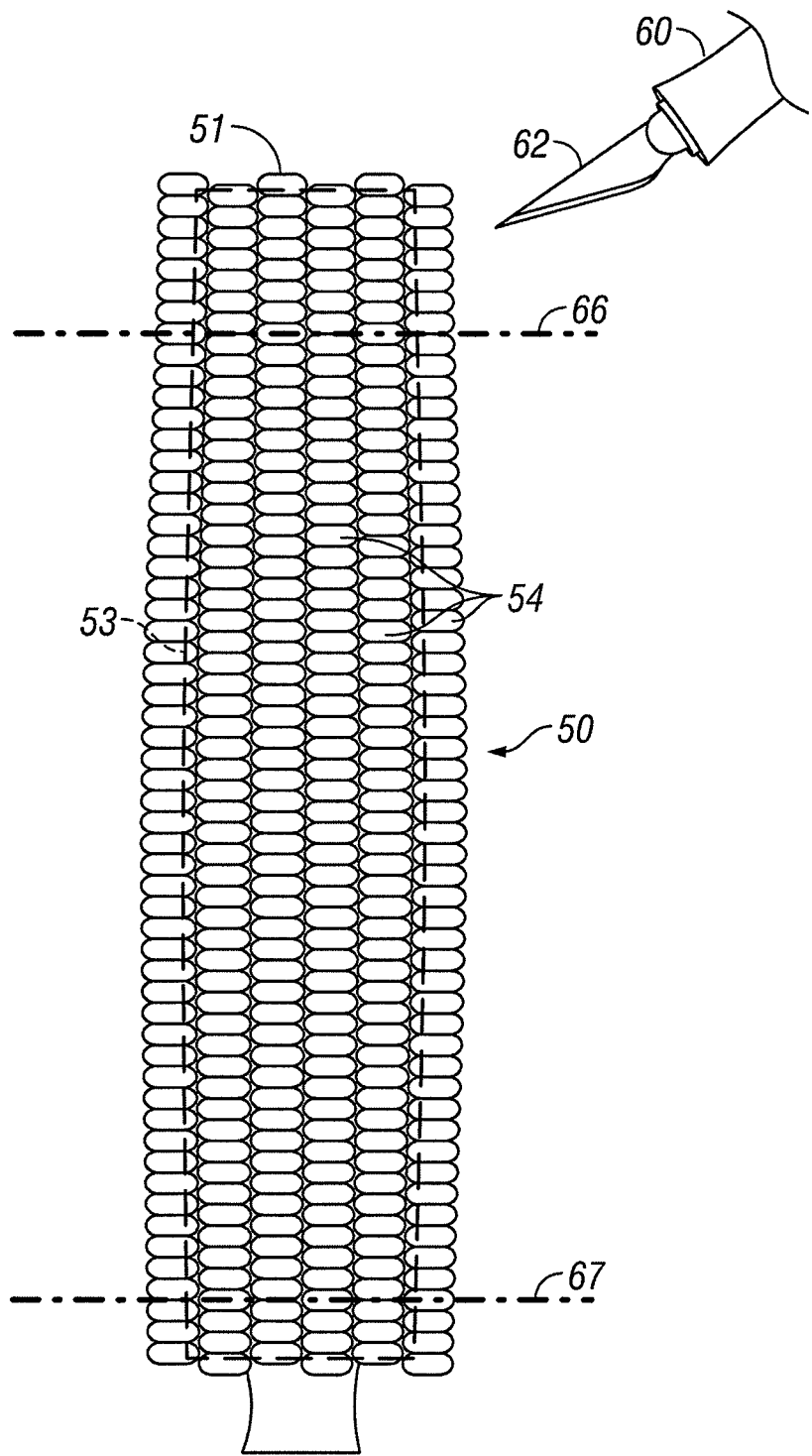
FIG. 5 is an enlarged side view of an ear of maize with developing kernels in place on the cob.
Figure 6:
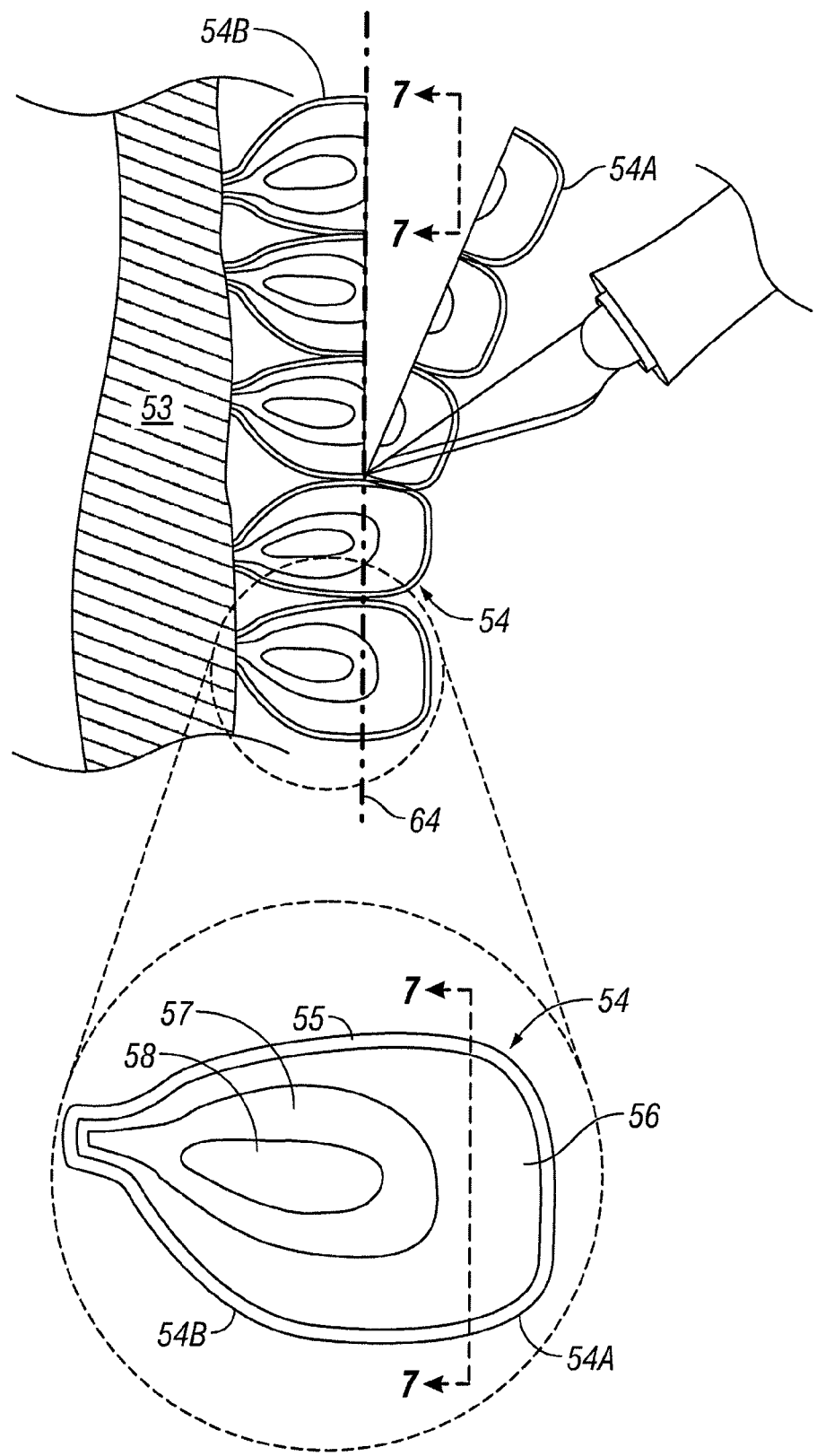
FIG. 6 is a further enlarged sectional view of FIG. 5 showing a method of exposing or gaining access to internal tissue or structure, including embryos, of multiple kernels attached to a cob; including a magnified view of a whole kernel indicating generally its various parts.
Figure 7:
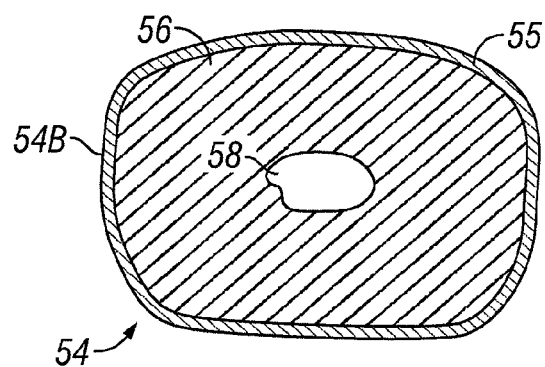
FIG. 7 is an enlarged sectional view taken along line 7-7 of FIG. 6.

FIG. 5 illustrates generally knife 60 with blade 62. This could be an X-acto™ type utility knife or any other suitable cutting instrument or tool. A worker can manually make cut 7-7 for each kernel 54. This can be done in a relatively short amount of time (e.g., a matter of no more than a few minutes, and with practice a matter of under a minute, perhaps even just seconds per ear).

As can be appreciated by viewing the Figures, the kernels are essentially radially and perpendicularly positioned relative the longitudinal axis of the ear. When the kernel crowns are removed, the internal tissues or structures are thus exposed in those directions. Removing by cutting minimizes fragmentation or generation of pieces of pericarp which might contaminate the sample.

For embryo extraction, at least the pericarp must be removed. It has been found desirable to not remove too much of the kernel. For example, it can be beneficial that no more than ½ of the kernel is removed by the cutting away of the crowns. This deters any damage or destruction to the embryo or its cells. As will be further described below, it also leaves more mass on the ear (and around each embryo) to generate more centripetal force, and thus more reactive or real centrifugal force to promote ejection or release of endosperm and embryo by overcoming the force or forces holding endosperm and embryo to the seed (e.g., the reactive force exceeds the tensile strength of any tissue or structure holding the embryo in the seed, or the reactive force exceeds any adhesive force tending to hold the endosperm or embryo in the seed). The endosperm comprises over 80% of the dry weight of a kernel.

Figure 11:
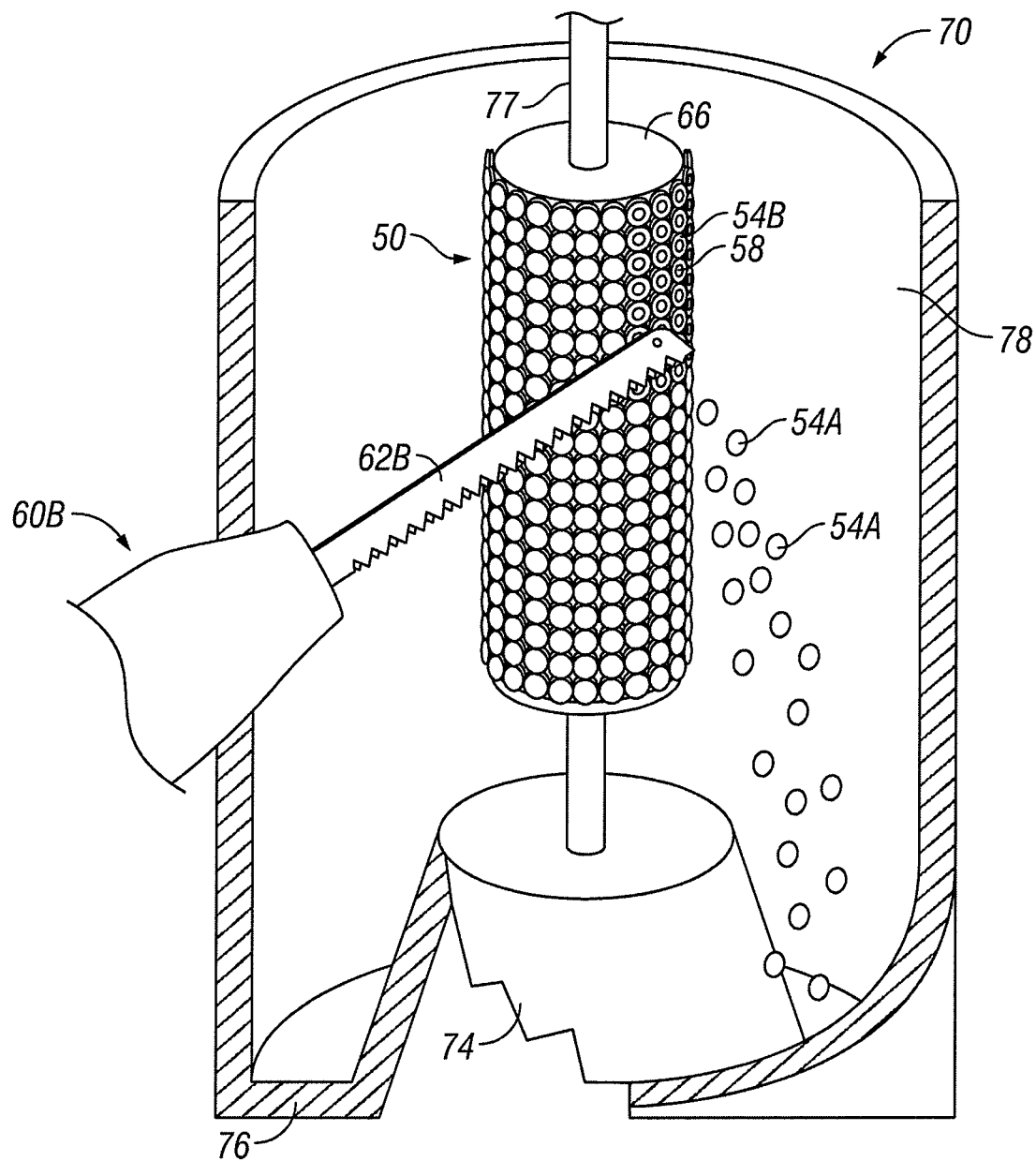
FIG. 11 is a partial cutaway perspective illustration of an alternative method of cutting kernels on the cob to gain access to the interior of the kernels.

Other methods to expose the seed interior are possible, as described earlier. FIG. 11 shows one method. An electric knife 60B with blade 62B could cut away the crowns 54A while the ear 50 is held on a rotatable or fixed spindle 77 inside an open top container 70. A worker can cut one vertical swath of ear 50 and then incrementally rotate ear 50 to a next swath of kernels. This can be repeated until all sides of the ear are cut to expose the embryos. The closed bottom 76 and sidewall 78 of container 70 would capture the crowns 54A for use or disposal. Ear 50 would then be processed and ready to be placed into blender 20. The spindle 77 can be elevated on raised portion 74. Other containers or ear holders can be fashioned as desired by the designer.

It will be appreciated that even more automated methods of cutting kernels on the cob can be utilized. One might be the use of a laser beam that would cut the swath. A stepper motor or another mechanized device could be used to rotate ear 50 for each swath cut.

Figure 8:
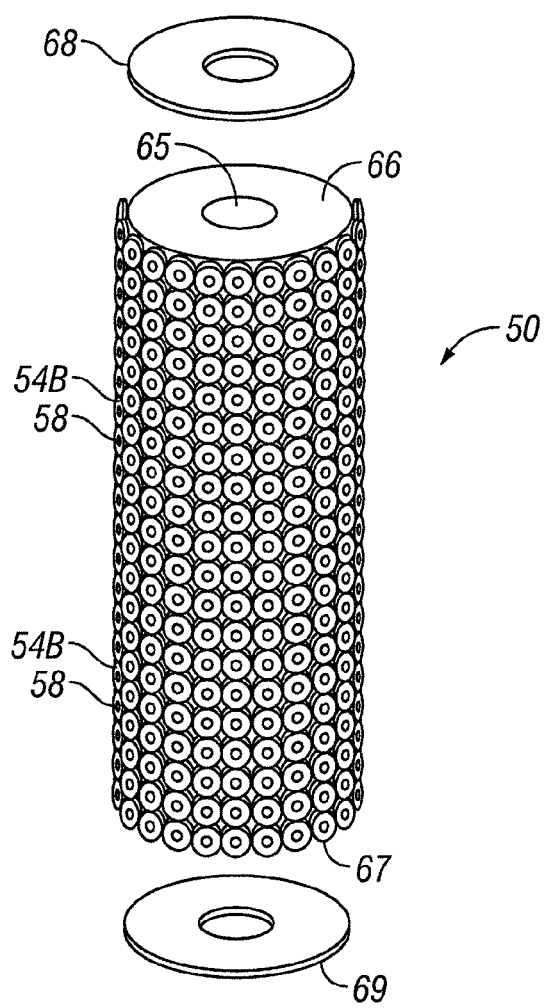
FIG. 8 is a perspective view similar to FIG. 5 but showing the ear of maize after cutting the crowns off the kernels to expose the interior of the kernels.

Once ear 50 is processed into the form illustrated in FIG. 8, plates 68 and 69 can be placed on opposite ends 66 and 67 of processed ear 50. A bore 65 can be drilled (e.g., with a standard drill press or hand drill) through the longitudinal axis of ear 50. Bore 65 may also be created using a longer bit in the automated ear boring apparatus shown and described in Provisional Application Ser. No. 61/153,543, filed Feb. 18, 2009, which application is assigned to the owner of the present application and incorporated by reference herein in its entirety. In this embodiment, bore 65 (e.g., approximately ¼ inch diameter core) is equal to or slightly smaller in diameter than the outside diameter of driven spindle 30. This allows ear 50 to be interference-fit upon and slid down driven spindle 30. Additionally, the multi-sided cross-section (e.g., hexagonal, ¼ inch flat to flat) of the exterior of middle portion 32 of driven spindle 30 would help hold ear 50 in place so that it would rotate in correspondence with rotation of spindle 30, even at relatively high rpm, such as is used in this embodiment. Plates 68 and 69 would help sandwich ear 50 in place on spindle 30. An example of an air jet is disclosed in published application US2005/0254053 entitled "Non-destructive single seed or several seeds NIR analyzer and method", assigned to the owner of the present application and incorporated by reference herein in its entirety.

This quick connect coupling spindle arrangement provides for firm but quick exchange of ears, and tends to compensate at least somewhat for the eccentric load it bears. An option would be to use a larger spindle to reduce eccentricity—to try to have the mass of the spindle dominate that of the ear.

The size of processed ear 50 of FIG. 8 is approximately 4 inches in length and one and one-half inches in diameter. In one example, bore 65 is one-quarter inch in diameter for a one-quarter inch outside diameter of middle section 32 of driven rod 30.

Blender 20 can be any of a number of standard commercial type blenders. One example is a Waring 3hp-3½ hp heavy duty, lab grade blender (Waring Commercial, 314 Ella T. Grasso Ave., Torrington, Conn. 06790 USA). Blender container 26 can be of various sizes but a one liter container is shown (it can be mounted with an adapter if needed). Blender 20 is rated at 47,000 rpm and has low, medium, high, and pulse selectable speeds. Blender 20 could be made programmable to ramp up or down in speed.

Motor 21 is operated at speeds between 9,000 and 50,000 rpm. It has been found that between 15,000 and 20,000 rpm seems to work well for ejecting immature embryos from maize seed. This has been found to generate between 500 and 6000 G on the seed. This promotes the ejection of the internal contents of the seed because their exposed ends are radial to the axial rotation of the ear. Each seed essentially rotates in a plane that is perpendicular to the long axis of the ear or spindle. Rotation subjects the seed to an acceleration field. Empirical testing allows selection of a speed which balances efficient and effective separation of embryo from kernels without destroying the embryos, but also without causing detachment of the kernels from the cob, disintegration of the cob or damage to the ejected embryos.

A benefit with a blender at these speeds is that the forces necessary for release of the endosperm/embryo from the kernel can be developed quite close to the rotational axis. Centripetal acceleration is a function of rotational speed and distance from the rotational axis. The natural structure of the ear of maize means that its kernels are quite close to the rotational axis. The relatively high speeds of a lab grade blender produce higher forces than if the ear were much larger in diameter.

The container around the ear to collect the ejected material can also be relatively close to the rotating ear and relatively small. In turn, this allows the entire machine to be relatively small in size. It does not require significant laboratory space or expensive machinery to create the necessary g-forces.

It is possible to alternatively sling or swing the ear in a circle. If ear 50 were slung in a large diameter circle, similar results could be achieved but it would require a large volume of space.

As is to be appreciated, in this embodiment, the endosperm of immature maize kernels is not solid and is somewhat liquid. The embryos are more compact and solid. It has been found that at the speeds or g-forces of this example, rotation of an ear around its long axis with kernel crowns removed results in the ejection of embryos and at least some endosperm, while the cob and remaining seed stays intact on the spindle. This was a surprising result because it was not anticipated that a tiny embryo, with a tiny mass, could get through the endosperm/starch and eject from the ear, without the remainder of the kernels becoming detached also and/or the cob disintegrating. But this also was surprising because the relatively large acceleration does not destroy the embryos or their cells.

It has been found that interference-fit of ear 50 on spindle 30 and rotation at the above-mentioned range of rpm produces sufficient reactive or real centrifugal force to cause immature embryos and at least some endosperm in maize seed to separate from the remainder of the seed, but does not cause separation of the remainder of the seed from the cob or break-up of the cob.

Cutting or shaving the kernel tops on an ear and spinning the ear on its long axis to use reactive or real centrifugal force to pull the embryos from the kernels is one aspect of this embodiment. The ends of processed ear 50 are held or clamped in place and the whole ear is rotated or swung like a sling so the kernel tops are tangential. This forces the embryos out. The ear is rotated to promote emptying of all embryos. In tests, essentially the entire ear has been depleted of embryos in a few minutes or after a few seconds. Blender 20 is basically a centrifuge. This embodiment pre-processes an ear of maize to sever the distal portion of the pericarp with the kernels attached to the ear and uses vectorial acceleration to extract the embryos from the kernels.

Real or "reactive" centrifugal force occurs in reaction to a centripetal acceleration acting on a mass. This reactive or real centrifugal force is equal in magnitude to the centripetal force, is directed away from the center of rotation, and is exerted by the rotating object upon the object which imposes the centripetal acceleration.

Centripetal force puts the ear in rotation about its longitudinal axis, which in this case is fixed. The centripetal acceleration varies with the radius r of the circle and speed v of the object, becoming larger for greater speeds and smaller radii. The centripetal force is applied perpendicular to the rotational axis, thus roughly directly radially into each kernel because of the natural relationship of maize kernels to the cob (each kernel extends generally radially and perpendicularly from the long axis of the cob or ear). Somewhat similar to a centrifuge, the centripetal acceleration on each kernel related to the centripetal force causing rotation of the ear (and thus the kernels on the ear), influences or ejects much of the internal tissue or structures of the kernel when the reactive or real centrifugal force overcomes the centripetal force holding the internal tissue or structure in the kernel while rotating. Specifically, it has been found that the attachment of the kernel to the cob of a maize ear is quite robust. Likewise, the external tissue or structure of the maize seed (i.e., the pericarp) is quite robust. Finally, the embryo is held in the seed by less robust internal structure and surrounded by endosperm, also less robustly connected internal tissue or structure. Thus, in a somewhat analogous manner to centrifugation, when an ear of maize is rotated about its longitudinal axis with the kernel crowns removed, at a certain point based on rotational speed and distance of the kernel from the rotational axis, the forces holding the embryo and endosperm to the kernel are removed, broken, or otherwise disrupted sufficiently, and the embryo and endosperm fly off the ear. In this example, with an ear roughly 1.5 inches in diameter, and the maize at an immature stage, it has been found that rotating the ear in the range of speeds set forth above in this example tends to influence release of the embryos of most kernels. It is perhaps more typical to specify the amount of acceleration applied to the kernels, as opposed to specifying a rotational speed such as rpm. Acceleration is often quoted in multiples of g, the standard acceleration due to gravity at the Earth's surface. This distinction is important because two rotating ears with different diameters running at the same rotational speed will subject kernels to different accelerations. The acceleration can be calculated as the product of the radius and the square of the angular velocity. Relative centrifugal force is the measurement of the force applied to a sample within a centrifuge. This can be calculated from the speed (rpm) and the rotational radius (cm) using the following calculation.

$$g = RCF = 0.00001118 r N^2$$

where
g=relative centrifuge force
r=rotational radius (centimeters, cm)
N=rotating speed (revolutions per minute, r/min)

It has been found that for immature maize ears of around 21 days after pollination g forces in the range of 500-6000 influence embryos and endosperm from within kernels with crowns removed.

Use of other gravitational forces such as orbital, vortex or those random in nature could also prove to be viable means of isolation of embryos and may have less impact on downstream viability of the embryo.

Optionally, ejection of embryos/endosperm could be accomplished by relatively quick deceleration. The kernels could be subjected to a deceleration field (e.g., rotating the ear 50 at relatively high speed and then quickly slowing it down). This also could lead to breaking or removing the centripetal or other forces (e.g., tensile, adhesive, or other forces) holding the embryo and endosperm to the kernels.

The objective of this embodiment is to allow for high throughput extraction of immature maize embryos. At this particular stage, the stem apical meristem should appear terminal and the silk scar is still evident on the distal portion of the kernel. The maize embryo is attached to the embryo sac near the micropylar opening by a column of cells called the suspensor, which eventually degenerates. At early stages of development, the zygote and the young embryo are covered by a cuticle. The endosperm becomes solid and digests away nuclear tissue approximately 100 hours after pollination. Approximately two weeks after fertilization, starch is being synthesized and accumulated. Starch grains become apparent in the distal portion of the kernel (crown) and progress towards the proximal portion of the endosperm. This anatomical isolation of the embryo will allow for a ready detachment of embryos through the mostly liquid endosperm.

Normally 10 to 60 seconds of rotation of the processed ear 50 results in separation and collection of sufficient embryo tissue. However, 10-15 seconds is usually enough at 15,000 to 20,000 rpm, and usually no more than 60 seconds. Different rotation speeds and times can be used for different seed, different seed maturity, or other factors. In the case of maize with immature seed, it has been found that a typical ear might have around 300 kernels. At approximately 10 seconds per ear, harvesting of embryos would greatly exceed the state of art manual level of embryo extraction that can range anywhere from as low as 600 embryos per worker per hour, and in the best case scenario, to as much as 800 embryos per worker per hour depending on the age, attained growth and stage of development of the embryos. It is to be understood that because the method is so quick, it is generally acceptable that less than 100 percent of embryos from each ear be harvested. For example, it is acceptable to have 100 embryos per ear harvested given the high throughput efficiency of the method. However, by appropriate procedures, which might take some additional time, most if not virtually all embryos can be harvested.

Thus, the embryos and some other seed tissues or structures are essentially extracted from the ear by reactive or real centrifugal force, and are isolated from at least most of the remainder of the ear by being thrown by the force outward to the wall of blender jar 26.

In embodiment one, whole maize ears about 10-15 days after pollination are placed in a container and the distal portion of the kernel is shaved by knife, blade, a laser beam, or other means. Then the container is subjected to angular acceleration and the ear within the container is rotated 360 degrees around its longitudinal axis. The embryos and some other materials expelled by the acceleration force are collected on the walls of the container and then removed (e.g., washed out into another container). The contents of this container can be dumped onto a density gradient tube and spun to separate the embryos from other kernel debris. Any of a number of sorting or filtering processes can be used to separate embryos from other materials. The embryos themselves could be filtered or sorted according to some parameter (e.g., size, density, weight, constituents, hydrophobicity, etc.). Another option would be to expose the embryos and other materials to brief secondary centrifugation in a liquid to separate materials by density. Still another option to improve embryo extraction rates and increase the number of intact embryos extracted includes the pre-extraction process of rolling the ear of corn on a flat, hard surface so that pressure or force is exerted on the hood surface of the ear without breaking the pericarp or rupturing the seed coat. This pre-extraction process is preferably performed prior to cutting off the cap of the kernels. The pre-extraction process of rolling the ear softens/weakens the endosperm to permit the rpm of the ear spinning apparatus to be reduced to ~9,000 rpm, which in-turn increases the number of intact embryos extracted. This pre-extraction process is highly effective especially where the endosperm has started to thicken in a more mature ear. The present invention contemplates other means in addition to rolling the ear for softening/weakening the endosperm or other internal tissue of the seed. For example, any device or apparatus configured to pulsate, vibrate or apply constant pressure or force to the kernels without rupturing the seed coat to soften or weaken the endosperm or other internal tissue are contemplated herein.

It is to be appreciated that blender 20 could be operated or be programmed to have a speed regime. For example, it could be ramped up gradually to top rotational speed and then ramped down. Other regimes are possible according to need or desire.

A specific example is as follows. Blender 20 can be operated for a first short period at a lower rpm (e.g., 10,000 rpm or lower yet if pre-extraction processes like rolling the ear are used) and then increased for the remaining duration to the 15,000 to 20,000 rpm or whatever speed is desired. As can be appreciated, rotation at such high speeds does produce substantial forces. Therefore, the worker should ensure, to the extent possible, that the drilled bore 65 through ear 50 is as near the rotational longitudinal center of ear 50 as possible and that ear 50 is as secure as possible. It has been found, however, that ear 50 does not need to be adhered or fastened to spindle 30 for blender 20 to operate adequately.

Bearing 48 can be of different types (sleeve, ball, etc.). There is normally a bearing at least at or near the bottom of spindle 30. Drive connection 40 allows quick coupling and uncoupling of drive spindle 30 for a quick and efficient exchange of ears 50 from sample to sample.

FIGS. 9A and B illustrate that stabilizer sleeves 84 and roller bearings 82 could be used at both ends of spindle 30, for additional stabilization of both ends and to take additional load off of each end of spindle 30. In the embodiment of FIGS. 9A-B, at least upper end 34 of spindle 30 has been found to place a substantial load on bearing 48. By placing the elongated sleeves 84 along each end of spindle 30 and journaling the outer end of each sleeve 84 in a roller bearing 82, spindle 30 is further stabilized during such high speed rotation.

Figures 10A, 10B:
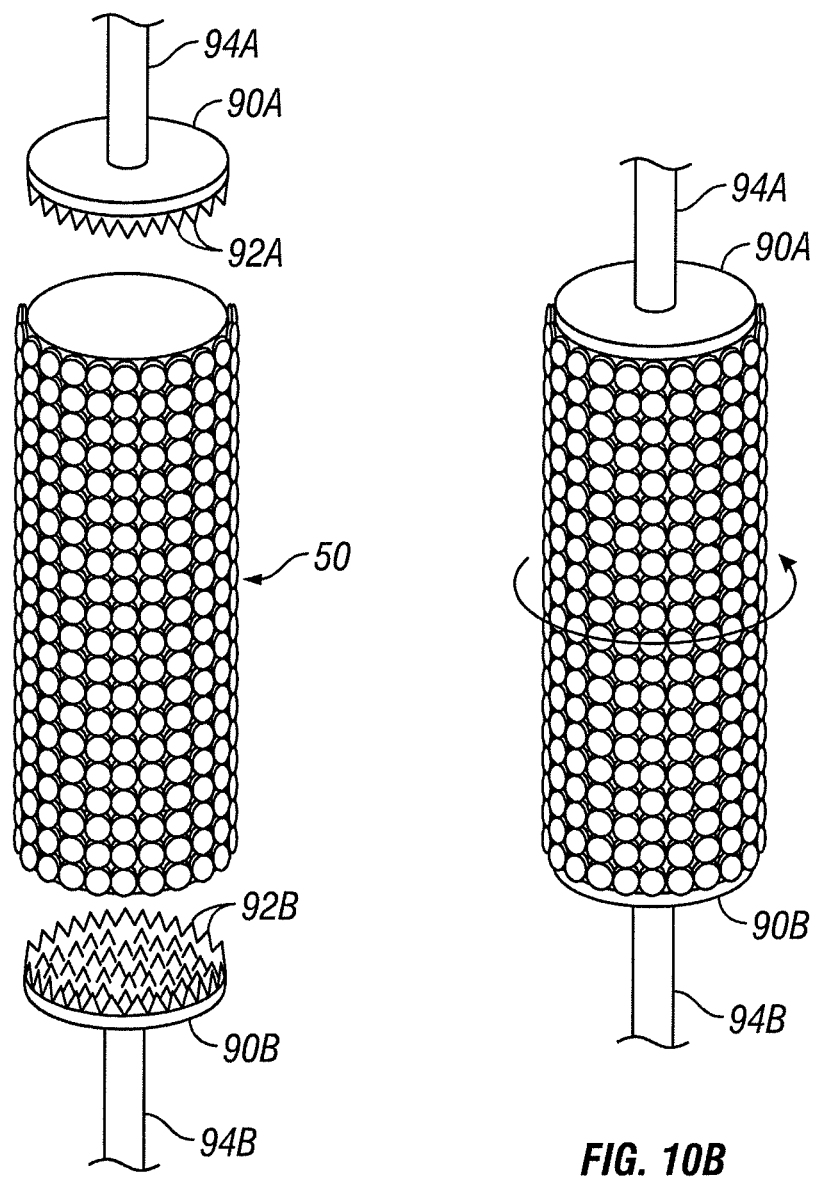
FIGS. 10A and B are diagrammatic views of an alternative way to secure an ear for rotation; here by clamping top and bottom and without a spindle.

An alternative mounting method for mounting ear 50 for high-speed rotation is illustrated at FIGS. 10A and 10B. Instead of coring the ear to receive a spindle, top and bottom plates 90A and 90B would be used to clamp opposite ends of ear 50. This would avoid the time and resources to core each ear. Teeth 92A and 92B, or other structure, could be used to help resist rotation of ear 50 relative plates 90A and 90B.

Plates 90A and 90B would be attached to axles 94A and 94B respectively, which could be operatively connected to a source of high-speed rotation.

Figure 2:
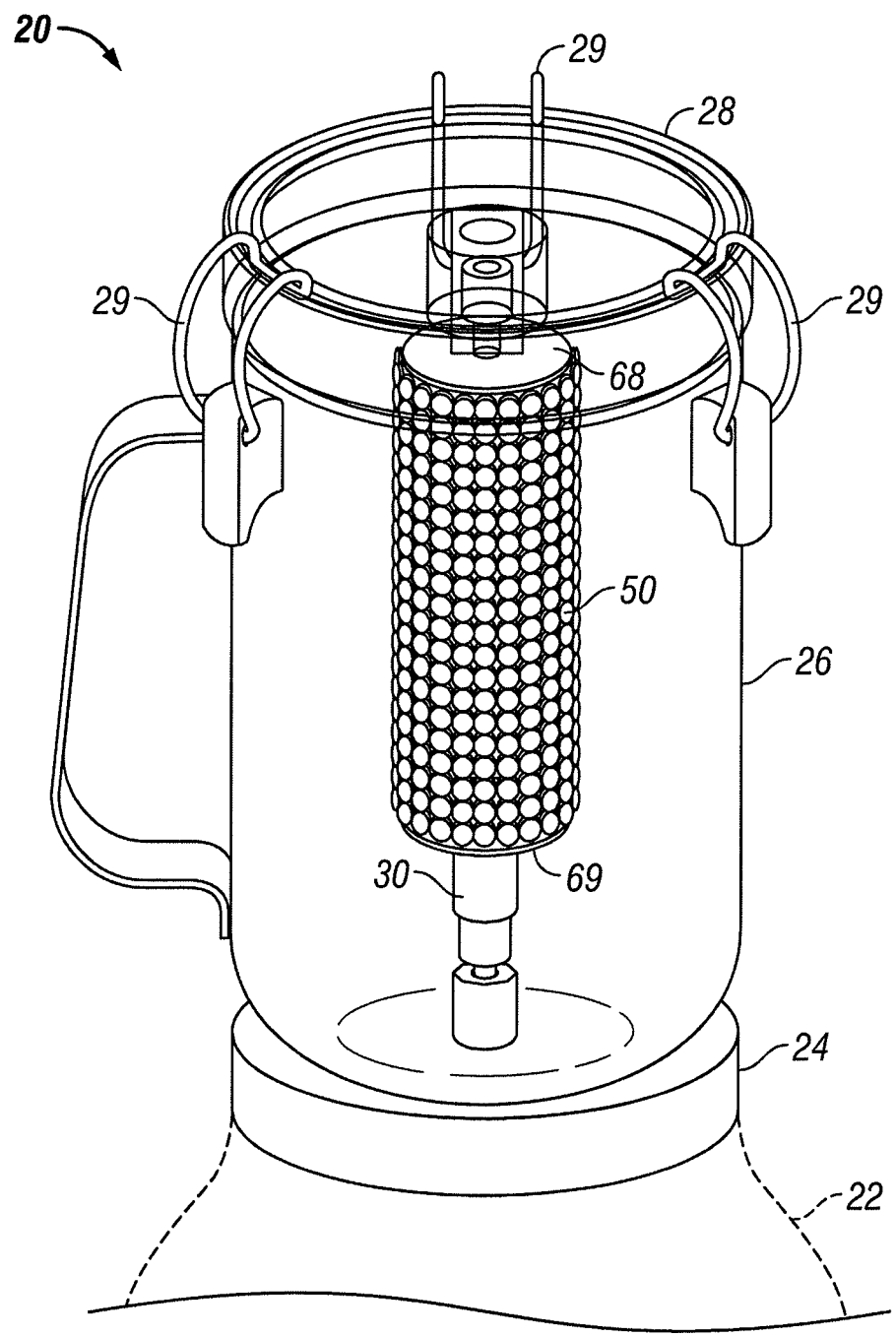
FIG. 2 is a perspective view of one exemplary embodiment of an apparatus according to the present invention, utilizing a blender-type device.
Figure 3:
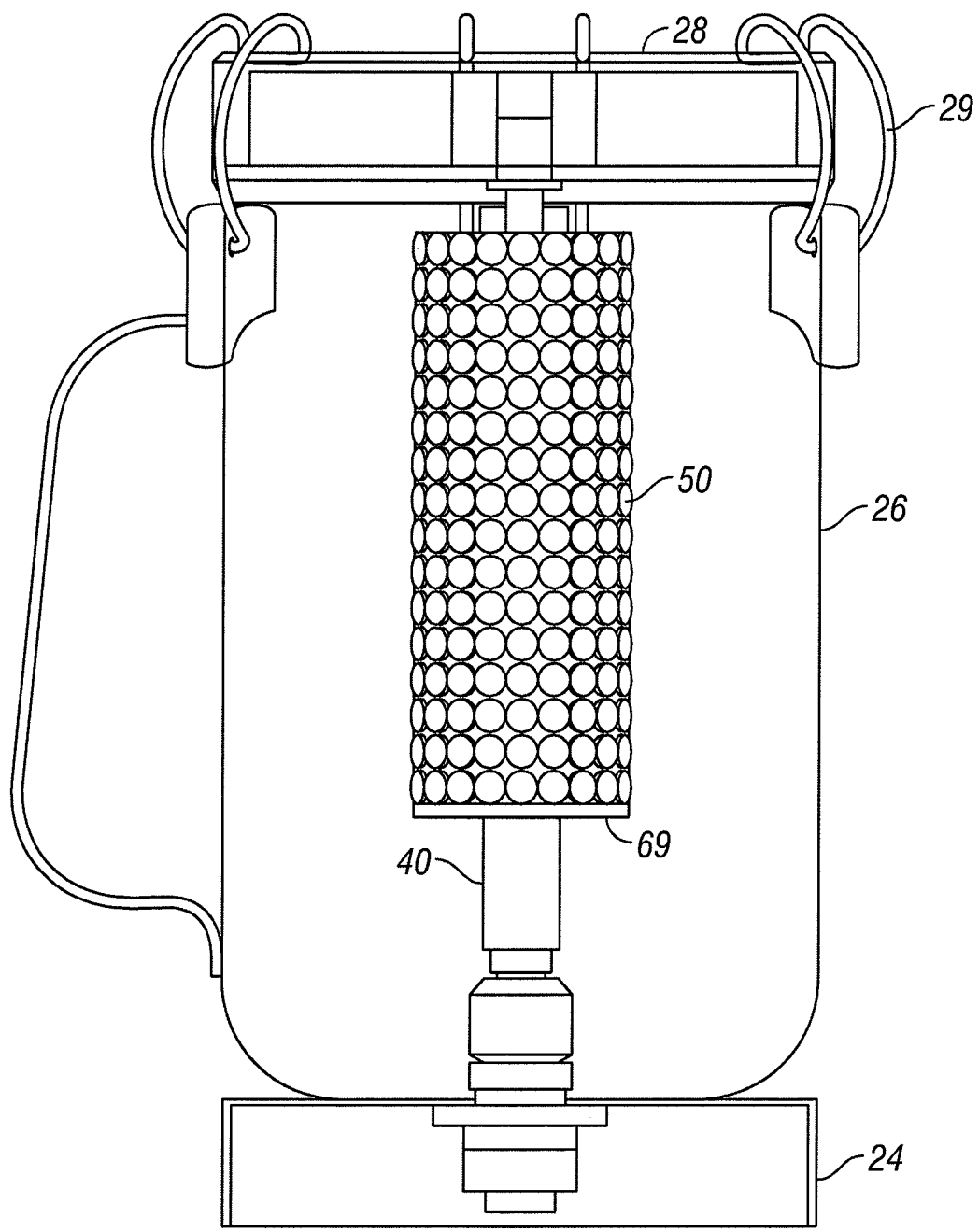
FIG. 3 is an enlarged front elevation of a portion of the device of FIG. 2.
Figure 4:
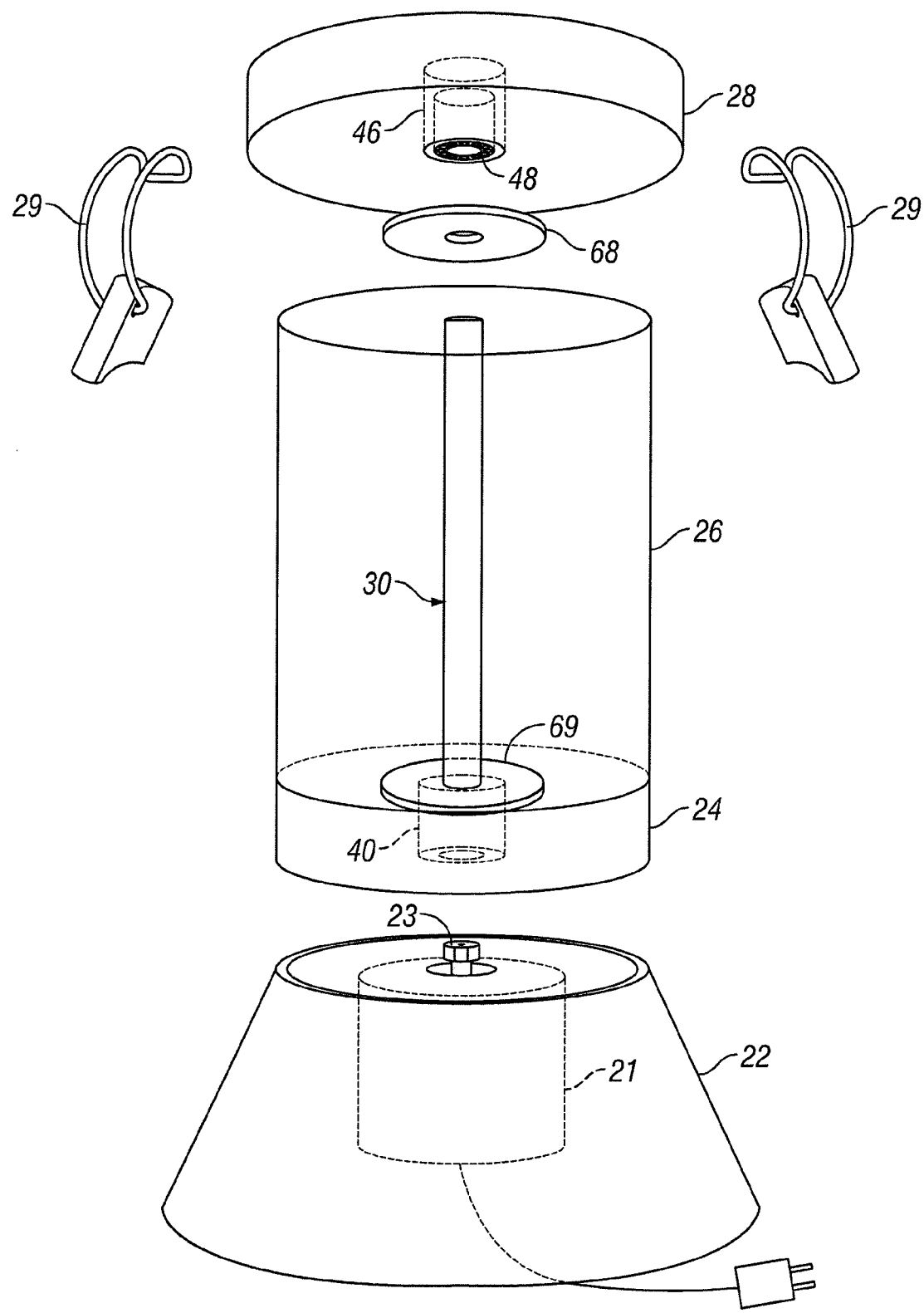
FIG. 4 is an exploded view of the device of FIG. 2.
Figure 12:
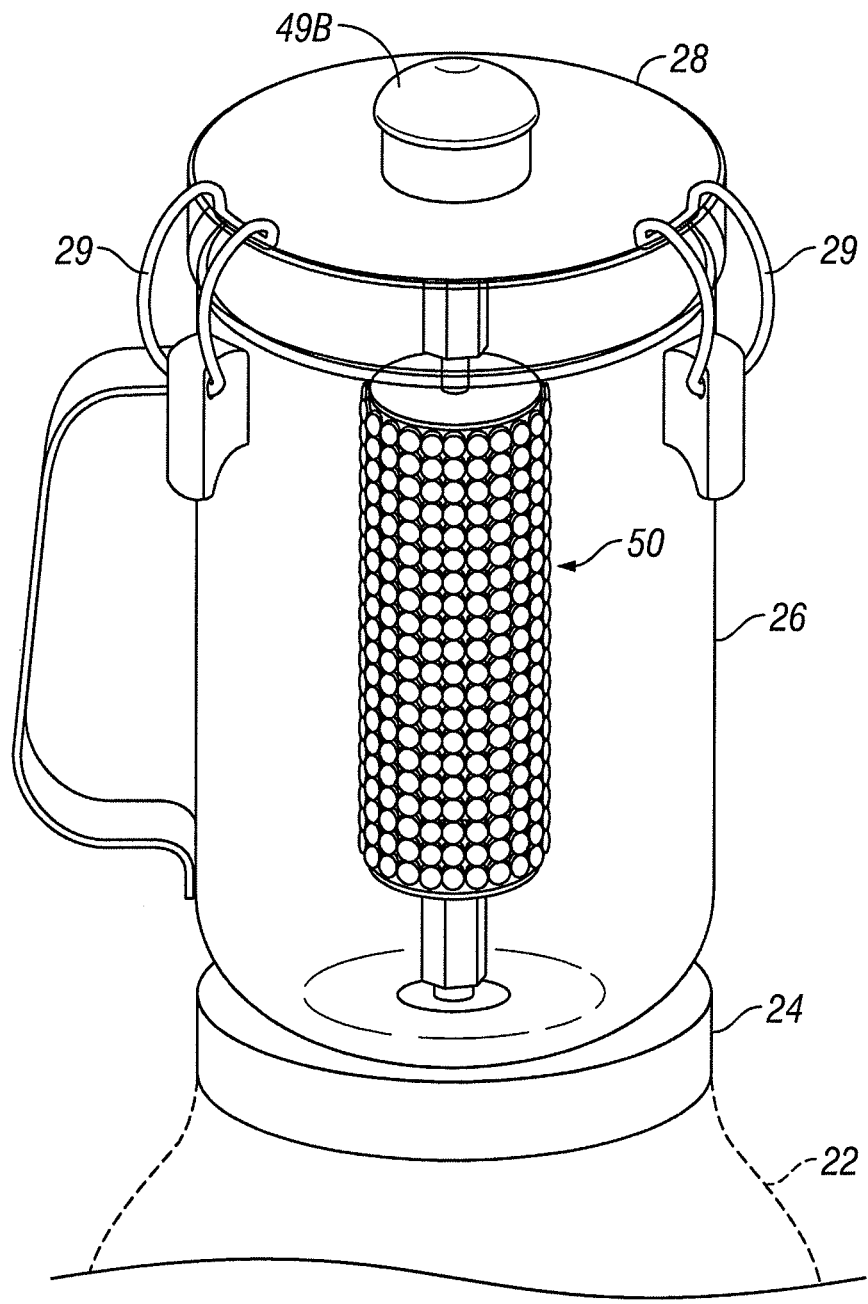
FIG. 12 is a perspective view of an alternative blender container assembly to that of FIG. 3.
Figure 13:
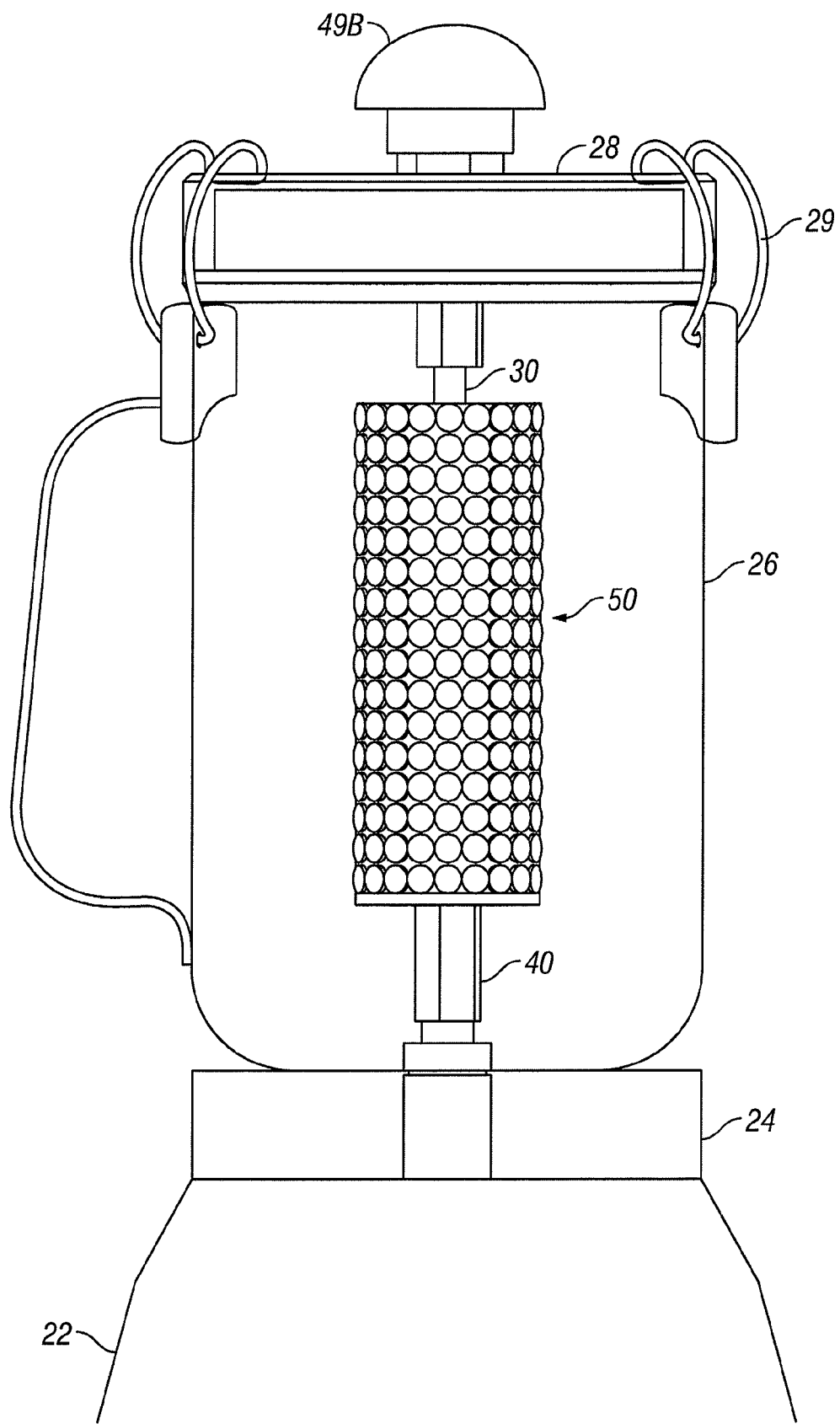
FIG. 13 is a front elevation view of FIG. 12.
Figure 14:
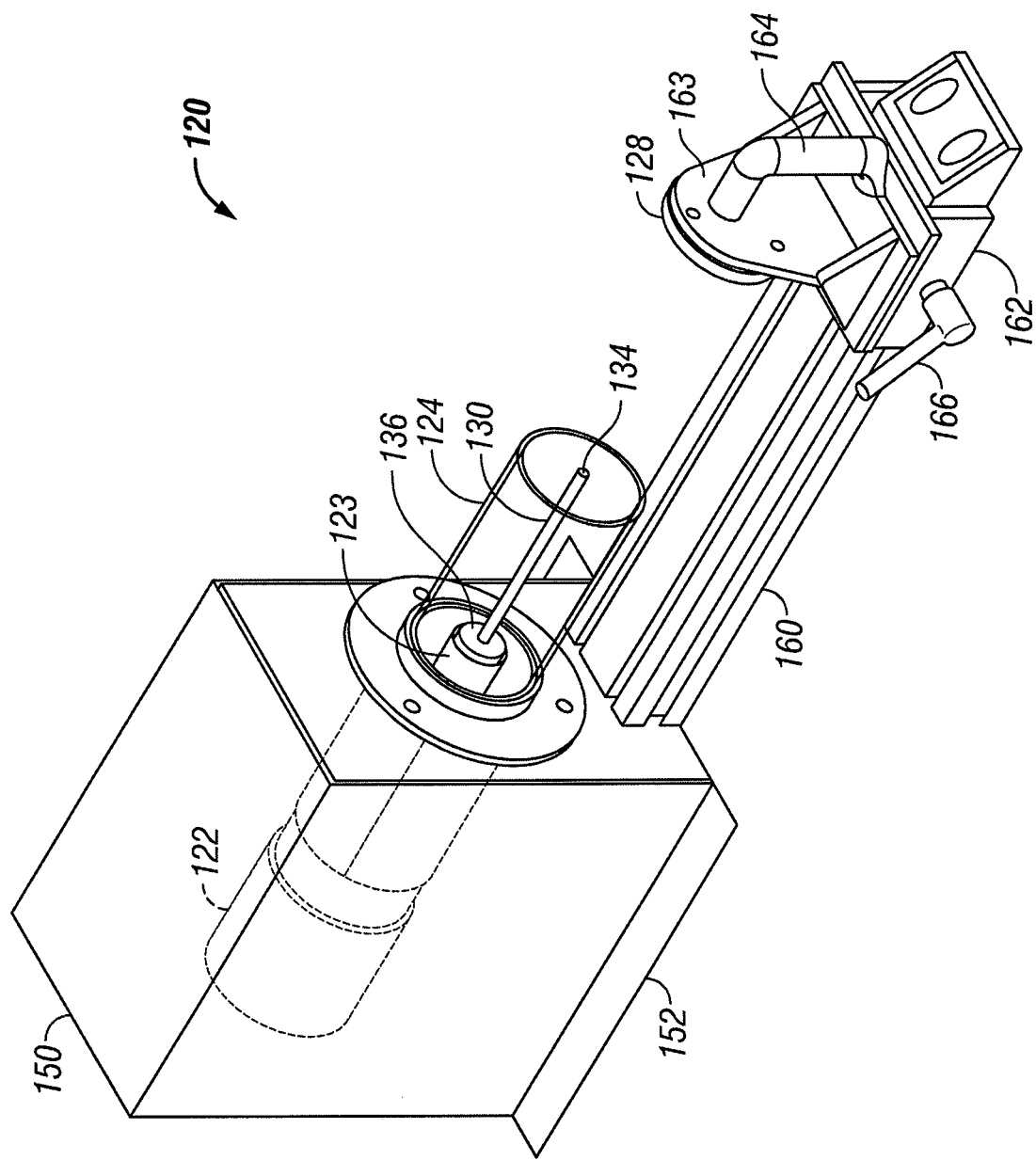
FIG. 14 is a perspective view of an alternative embodiment and apparatus similar to the embodiment of FIGS. 2-13 but utilizing a router as a source of rotational power.
Figure 15:
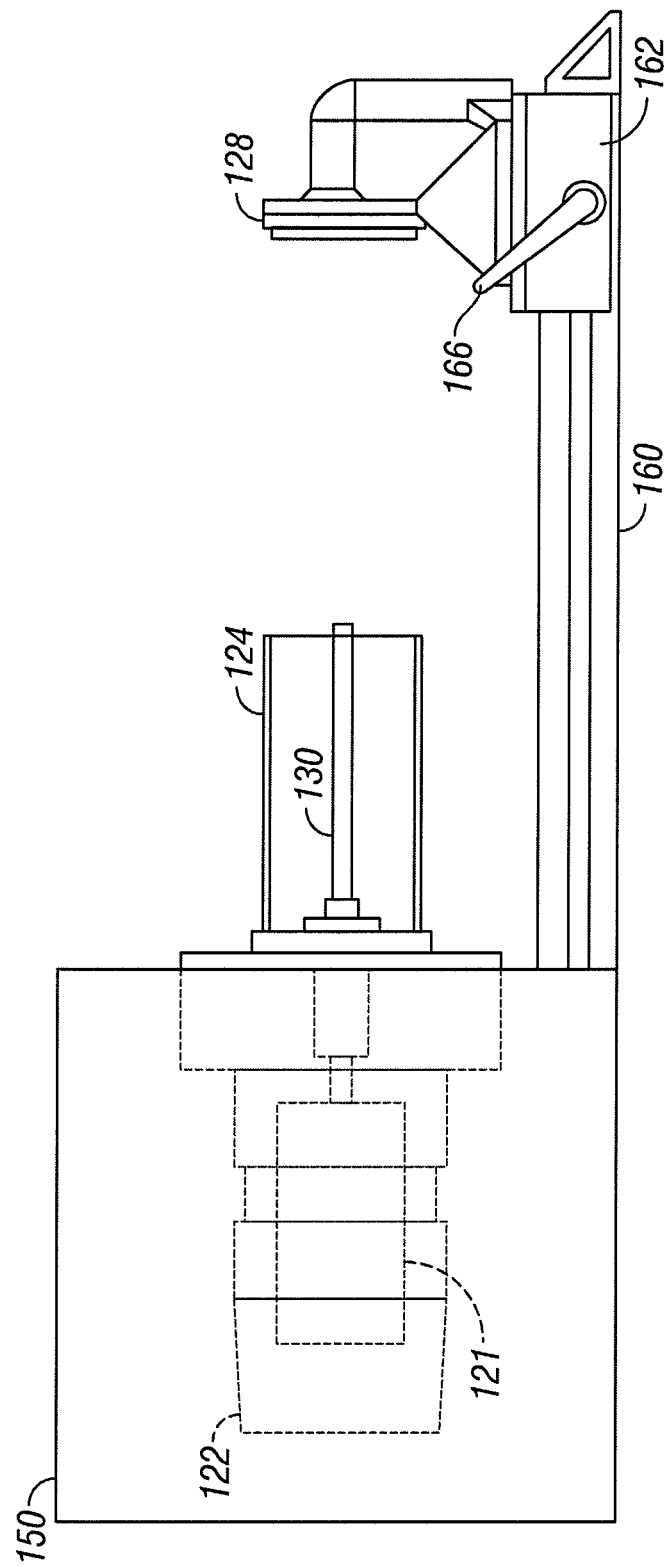
FIG. 15 is a side elevation view of FIG. 14.

FIGS. 12 and 13 show a slightly different embodiment than that of FIGS. 2 and 3. Instead of an internal bearing 48 in lid 28 of blender container 26, FIGS. 12 and 13 show an external bearing 49B. The driven shaft 30 would extend through an opening in lid 28. The external bearing 49B would be mounted on the exterior of lid 28. This would have lid 28 assist in providing stability to rotating spindle 30. Other means of stabilizing and providing bearing surfaces for spindle 30 are possible.

Other ear 50 rotation methods are possible. For example, ear 50 could be enclosed in a cylindrical container with ear 50 constrained inside. The whole container could be rotated at high speed (like a washing machine tub). Separation between ear 50 and the wall of the container could be maintained by spring-loaded or mechanical supports to hold ear 50 fixed allowing acceleration of the ear and to maintain a gap with the container wall to allow recovery of the embryos.

As can be appreciated, the sides of container 20, and thus the length of rod 30, can vary. The example shown in FIGS. 2-12 has one ear 50 on spindle 30. An option, if the spindle length allows, would be to place two processed ears 50 end to end on spindle 30. Another option is to have multiple spindles with ears 50 installed, ready to be interchanged into the blender. In the spirit of processing multiple ears with a single system at the same time, the present invention contemplates that anyone of the apparatuses described herein may be configured so as to provide parallel processing or multiplexing of multiple ears for extracting a greater volume of embryos simultaneously. In one aspect, an apparatus is configured to allow mounting and rotating of several ears simultaneously. For example, multiple shafts could each be driven by an individual motor all connected to a singular platform. In another aspect, one motor could be configured to power multiple shafts via pulleys or gears for simultaneously spinning multiple spindles configured into a singular platform. Any of the aforementioned configurations would enable the rotation of multiple ears at the same time. As part of these configurations, each ear on a shaft could be housed in its own vessel for collection, or more than one ear could be enclosed in the same collection vessel. Any of the apparatuses or other similar configurations of the present invention are capable of higher throughput and greater efficiency as compared to processing a single ear at a time. The benefit stems from the fact that more embryos are capable of being released and collected in the same time period required to process a single ear. Similarly, the motor in a parallel or multiplexing configuration could be powered using the same or less energy. Another configuration for spinning multiple ears simultaneously could include a longer spindle and collection chamber whereby 2 or more ears are positioned end to end on the same spindle such that the embryos are simultaneously extracted from the ears be rotating the spindle or by subjecting the ears to the same rotational forces. These and/or other similar configurations for parallel and simultaneous embryo extraction from multiple ears are contemplated by the present invention.

Once the sample has been collected in blender container 26, blender motor 21 is stopped. Lid 28 is unclamped, ear 50 removed, container 26 lifted from blender base 22, and the ejected embryos and other internal tissue or structure material is removed.

In one example, one or more embryos are extracted from blender container 26 one at a time with tweezers or another suitable gripping tool. This deters damage to the embryo and is a satisfactory method if only one, a few, or certain ones are desired. Alternatively part or all of the extracted embryos could be scraped out with a spatula or other tool, although this increases the risk of damage. However, even with a spatula, maintenance of viability of the embryo or its cells has been found to be at least on par with industry standards using conventional embryo extraction methods.

In another example, the interior of blender container 26 could be washed out with liquid such as ethanol, sterile water or 15% sucrose to suspend the embryos in the fluid and move the fluid suspension into another container such as a Petri dish, vial or lab plate. Blender container 26 can then be washed and sterilized and be ready for insertion of the next ear 50 for a next sample. The extracted embryos may then be moved into contact with a doubling agent and cultured in the agent for providing a doubled haploid embryo for producing doubled haploid plants, such as where the doubled haploids are transferred to a germination media for growing a doubled haploid plant.

Another option would be to line the inside of blender container 26 with a layer of substance or material. Examples could be a gel, a film of liquid, a plastic, a sheet material such as Saran Wrap®, or a craft foam sheet. The layer could be removable and with or without an adhesive. This layer could help collect the embryos as they fly off of ear 50. The liners could also deter damage to the embryos by providing a more cushioning material than the interior wall of the blender container. After spinning of ear 50 is complete, the layer can be removed and desired embryo tissue removed from the layer. Another alternative would be to use a stream of air as a layer to cushion the ejected embryos. The stream of air could also be used to transport the collected embryos to another container or location.

As mentioned, the user can select one or more embryos or all the embryos that have been extracted from the ear. The embryos may have to be separated from other materials (e.g., endosperm or debris). If multiple embryos are collected, they could be further processed. For example, the embryo material could be sized, e.g., by sizing it through a sieve. It has been found that embryo tissue of between 1.3 and 1.7 millimeters in length tends to be viable and useful. Other sizing or sorting methods could be used (e.g., any discrimination including but not limited to size, density, shape, surface nature and/or composition).

Embodiment 1 therefore allows for relatively high throughput of multiple ears 50 by (a) allowing quick exposure of multiple embryos on ear 50 by quickly cutting away the crowns of each kernel 54 while attached to cob 53, (b) quick mounting of processed ear 50 in blender 20, (c) operation of blender 20 for a relatively short amount of time to influence out or expel embryos from ear 50, and (d) quick and easy removal of one or more of the embryos. These steps can be repeated for a plurality of ears at the user's election. The user can implement conventional procedures to maintain identity or correlation of any embryo with its ear or plant. The extracted embryos may then be moved into contact with a doubling agent and cultured in the agent for providing a doubled haploid embryo for producing doubled haploid plants, such as where the doubled haploids are transferred to a germination media for growing a doubled haploid plant.

Exemplary Embodiment 2

FIGS. 14-17 illustrate an alternative embodiment 120 to that of embodiment 1. As can be seen from the figures, it utilizes a very similar technique for exposure, extraction and collection of embryos. Its major differences are as follows.

Instead of rotation of the processed ear 50 along a vertical axis in a blender-type device, it is done along a horizontal axis. As can be appreciated, rotation could be at any orientation depending on orientation of the axis of rotation of the structure of the machine that holds the ear. Spindle 130 is driven by an electrically powered rotational device 122. In this embodiment, device 122 can be a hand-held or a commercial table router having a drive shaft 123 and a chuck 136. The hexagonal geometry of shaft 130 can be mounted and secured for rotation in router chuck 136 by conventional means. A typical router chuck or collet has structure to allow quick connect/disconnect of a spindle (e.g., hex key with ¼ turn) to, in turn, allow efficient serial processing of ears 50. A housing can be added around the router for sound dampening.

A Plexiglas™, polycarbonate, plastic, or glass tube 124 can be mounted (e.g., held in position, adhered, or fastened) at one end to a housing 150 around router 122 and extend concentrically around shaft 130. Router 122 can be supported in housing 150 by a suitable support structure 152. Tube or container 124 is selected to be spaced from ear 50 sufficiently to collect the ejected materials and not allow the rotating ear 50 to strike them.

Device 120 includes a rail 160 extending parallel to and underneath spindle 130. A lid or closure 128 is mounted on carriage 162 that slides along rail 160. Closure 128 is held on rail 160 in correspondence with tube 124 by a plate or arm 163. Support 164 can assist in the structural rigidity of plate 163.

Figure 16:
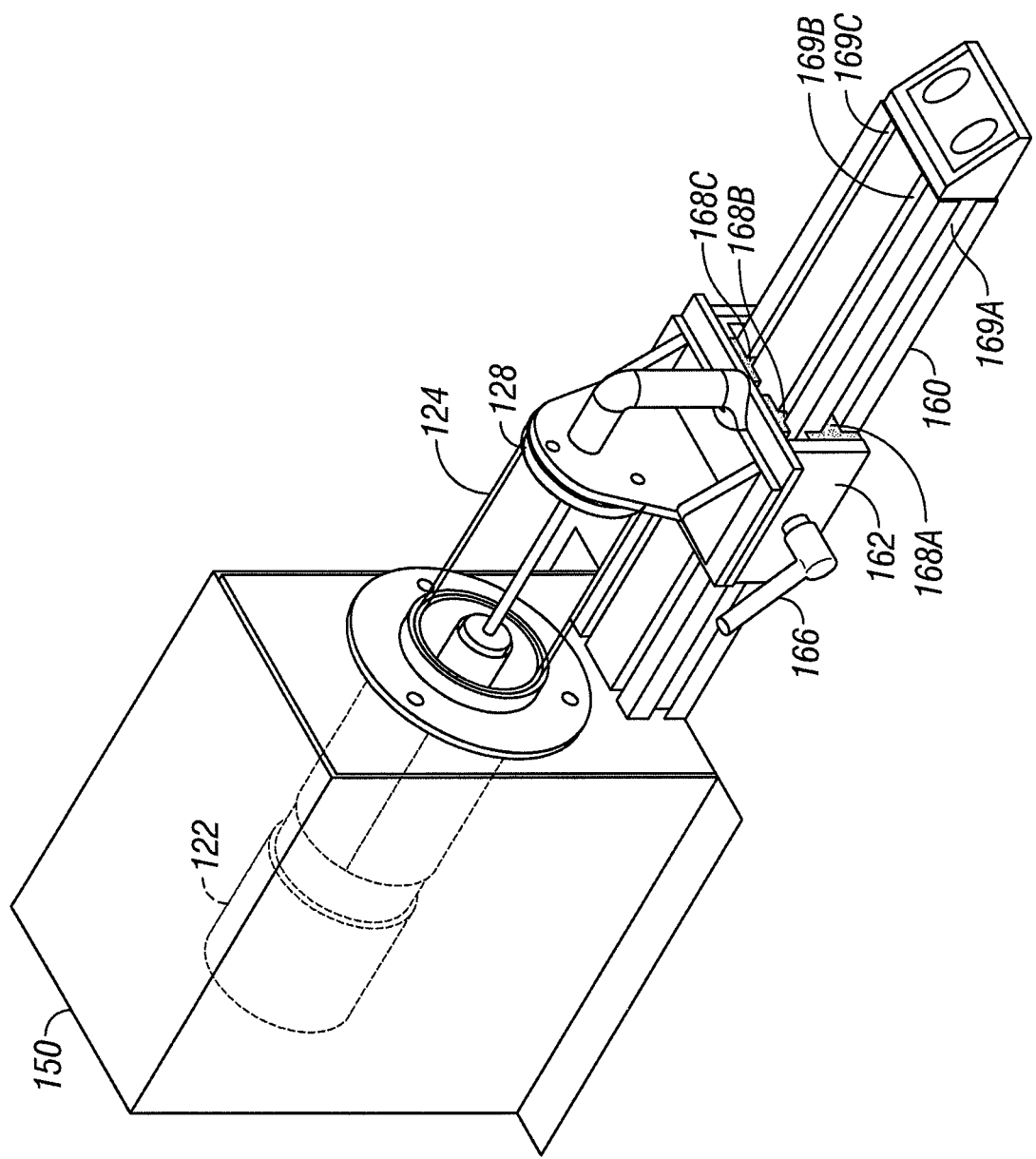
FIG. 16 is similar to FIG. 14 but shows the apparatus in embryo extraction mode (ear not shown).

As shown in FIG. 16, four T-members 168 (T-shaped-in-cross-section) are attached to interior bottom walls of carriage 162 and have flanges that mate into corresponding slots 169 in rail 160 (three T-members 168A-C and three slots 169A-C are shown in FIG. 16—the fourth pair, not shown, would be opposite from T-member 168A and slot 169A). The orthogonal relationship of some of these members and slots 168/169 holds carriage 162 against all but a sliding movement along the longitudinal axis of rail 160. The flanges in slots 169 assure very accurate sliding movement.

Figure 17:
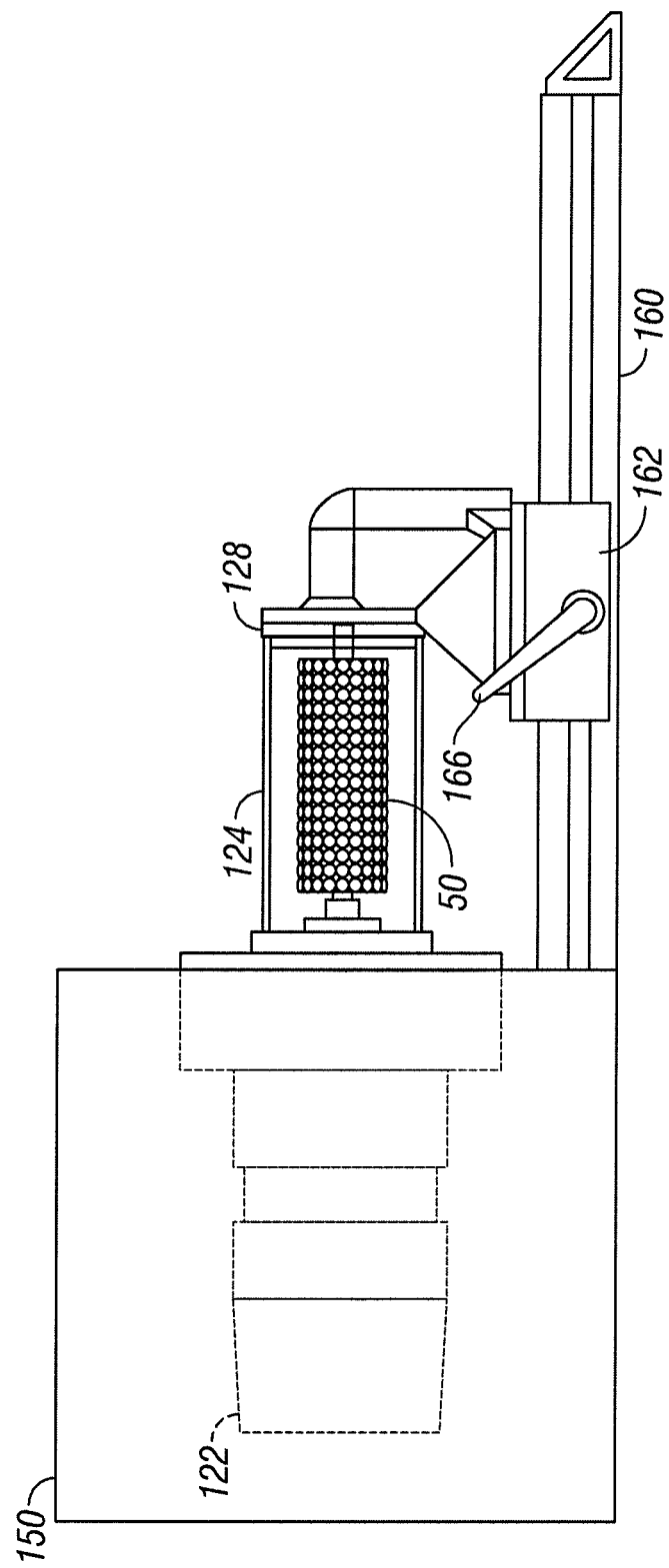
FIG. 17 is a side elevation view of FIG. 16 (ear shown).

Carriage 162 can be moved to its distal position (FIGS. 14 and 15), to allow the processed ear 50 to be slid onto spindle 130. As shown in FIGS. 16 and 17, the operator could then move locking lever 166 to an unlocked position and slide carriage 162 so that lid 128 mates with, covers and enters the open end of tube 124. Locking lever 166 can be moved to a locked position to hold lid 128 in the position shown in FIGS. 16 and 17. Locking lever 166 could operate, for example, a cammed or other type of releasable locking mechanism. The lid could include a bearing for the spindle.

Other types of constraint for the carriage or its lid are, of course, possible. Examples include interference-fit or some motion control device with locking brakes which hold the components in place when not energized. Also the lid can translate axially or in other directions relative to the tube. For example, it could move in a rotary or linear manner relative to the opening of the tube it covers.

Router 122 could be operated at the same speeds as blender 20 or higher. In this example, top speeds of over 30,000 rpm (with some routers up to 45,000 rpm) are possible. A bearing could exist in the end cap or lid 128 in which end 134 of spindle 130 would rotate. However, performing the pre-extraction process of rolling the ear on a hard surface increases the number of extracted embryos obtained while reducing the rpm necessary for extraction especially in the case where the ear is more mature. For example, a high percentage of intact embryos are extracted by rolling the ear, which also allows the machine rpm to be reduced to ~9,000 rpm.

Housing 150 could serve as a noise dampener for router 122 when in operation. Chuck 136 could utilize a chuck key. One quarter turn and spindle 130 could be tightened in place. Also, in either embodiment 1 or 2, a fume hood or laminar flow hood could be placed around the entire device for sterility purposes.

As with Embodiment 1, processed ear 50 of FIG. 8 could be rotated for a given, relatively short period of time. Embryos would separate from ear 50 by reactive or real centrifugal force and be retained and collected in tube 124. Embryo tissue material could then be removed manually or by some method or means. For example, one option to remove the embryos (and any other ejected materials) out from container 124 would be an automated means such as a vacuum. The embryo tissue material could be further processed. The extracted embryos may then be moved into contact with a doubling agent and cultured in appropriate media for providing a doubled haploid embryo for producing doubled haploid plants, such as where the doubled haploids are transferred to a germination media for growing a doubled haploid plant.

Embryo tissue material could be rinsed off or suspended in a fluid for collection and subsequent isolation. It could be passed through a sieve to select a certain size of tissue. The whole extraction process could take place in a fume hood for sterility. The collected material could be conveyed in solution to a purification filter to remove the embryos from other materials.

Embodiment 2 also pre-processes the maize ears by cutting away of kernel crowns to expose the kernels' interiors while still on the cob. Embodiment 2 also uses rotation of the processed ear at relatively high speed to extract the embryos from the ear and collect the extracted embryos in a concentric container. Once extraction is completed for an ear, that ear can be quickly and easily removed by reversing the process described above. Router 122 would be shut off, locking arm 166 released, carriage 162 slid away from housing 150 to expose the interior of tube 124, and embryo tissue could be removed. The remaining ear would also be removed, the interior of tube 124 and the surfaces adjacent to it on device 120 could be cleaned, and device 120 would be ready for the next sample ear.

Embodiment 2 relies principally on reactive or real centrifugal force and the specific structure of a maize seed to separate embryos from the seed non-destructively.

As can be appreciated, there could be a variety of ways to mount an ear and rotate it at speeds that result in embryo extraction and collection non-destructively to provide for doubled haploid plant production. The examples of Embodiments 1 and 2 are shown but there are several possible ways to achieve this objective.

Those skilled in the art will recognize that modifications, alternatives, and variations are possible to achieve the results of Embodiments 1 and 2. And further, those skilled in the art will appreciate that Embodiments 1 and 2, and variations thereof, can be applied in analogous ways for separating other tissue or structure from maize seed (e.g., endosperm), or embryos of other types of seed, or other tissue or structure of other types of seed, if such tissue or structure tends to separate under centrifugal action.

As can be further appreciated, other forces or methods exist that would allow exposure and/or extraction of specific tissue or structure from a seed for other tissue or structure of a seed. Several are mentioned with respect to the general method of FIG. 1. Several specific examples will be described later in further exemplary embodiments.

Exemplary Embodiment 3

Figure 18A:
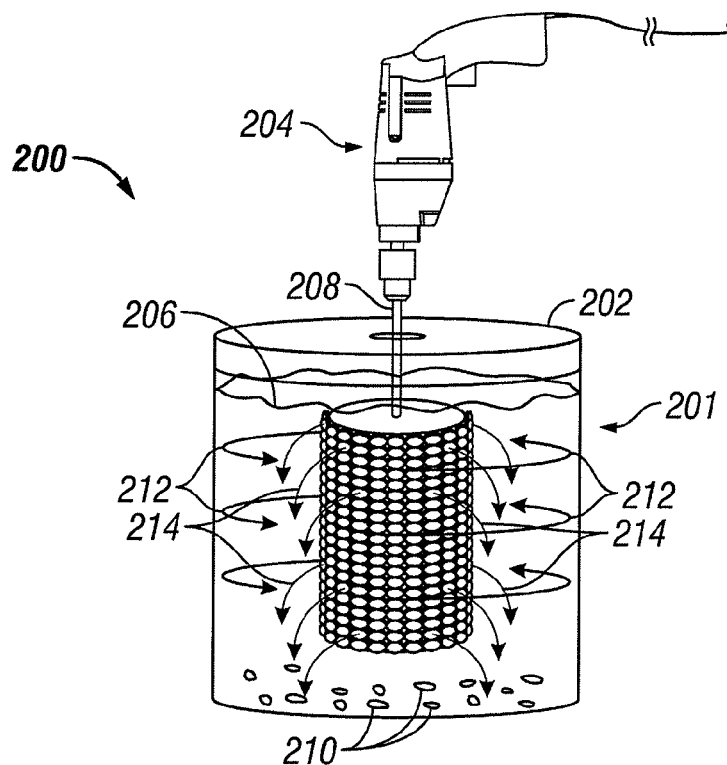
FIG. 18A is a still further alternative embodiment according to the present invention using a drill as a source of rotational power.
Figure 18B:
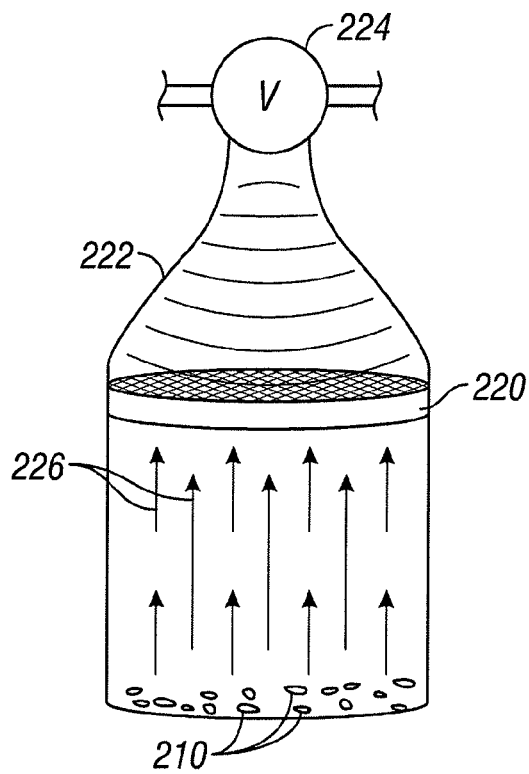
FIG. 18B is an illustration of an optional system to remove and isolate embryos after extraction from the ear with the assembly of FIG. 18A.

FIGS. 18A and 18B illustrate an alternative use of centripetal acceleration for embryo harvest. In this embodiment 200, an ear 50 (pre-processed to remove kernel crowns) is operatively attached to an axle 208 (as shown) installed in the chuck of electric drill 204 and rotated at relatively high speed in a liquid-filled container 201. Alternatively, the source of rotation and centripetal force could be a router or blender.

Liquid 206 can be sterile water or 15% sucrose. Embryos and other internal tissue or structure 210 would be ejected radially (see arrows 212) by centrifugal action sufficient to break the bonds of the embryos/endosperm with the kernels and propel those materials into liquid 206. The bonds of the embryo/endosperm could be broken, weakened or softened prior to extraction by rolling the ear on the hood surface without rupturing the pericarp and/or seed coat. The liquid would slow them down the ejected embryos thereby preventing damage and keeping the embryos intact. The embryos and other ejected materials 210 would fall by gravity (see arrows 214) to the bottom of container 201. The ejected materials 210 are then available for collection (container 201 can include a removable lid 202).

FIG. 18B illustrates that after collection of materials 210 as shown in FIG. 18A, the drill and ear could be removed. A filter 220 could be substituted for lid 202. A vacuum hood 222 in operative communication with a vacuum source 224 could be assembled as shown and then operated. Filter 220 can be selected to filter out or block embryos but allow passage of liquids and endosperm 210 and other smaller debris as shown by arrows 226. Embryos would then be collected and isolated on filter 220 and available for further use.

Exemplary Embodiment 4

Another approach would include the use of rotating bristles or brushes to break the seed coat and comb the embryo from the less formed endosperm. Contents would be brushed into a general collection area which might include a fine screen. The individual embryos could be rinsed on the fine screen while the endosperm material is washed through the screen. Vacuum sources may also aid in this process. As proposed, this process could also be useful for sizing of embryos.

Figure 19:
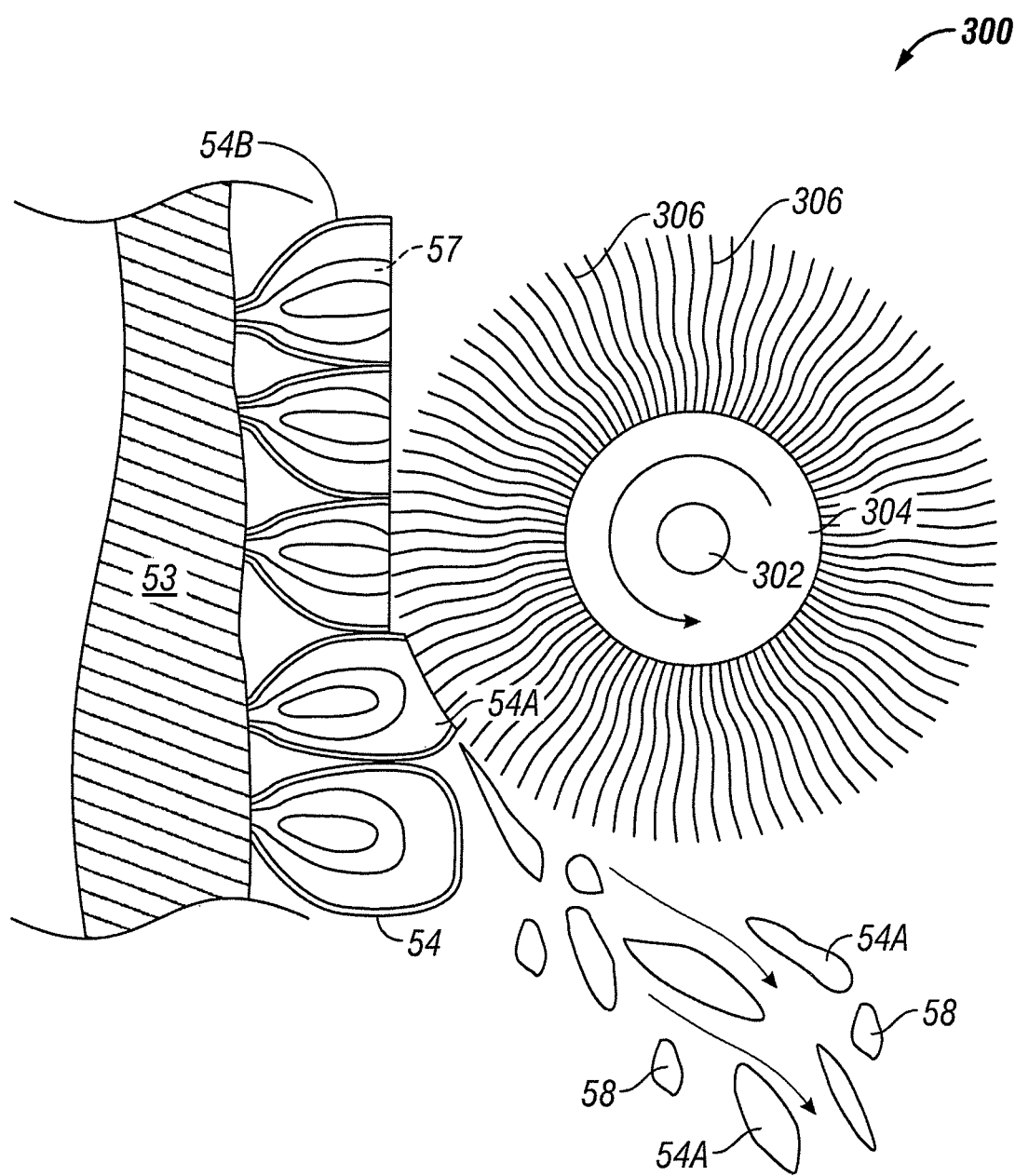
FIG. 19 is a still further alternative embodiment of the invention using a brush to grind or erode the seed exterior to gain access to its interior.

Such a potential embodiment is illustrated in FIG. 19. A wheel 304 would be rotated by a motor via drive shaft 302 in the direction shown in FIG. 19. Bristles 306 on the perimeter of wheel 304 would be brought into contact with kernels 54 on cob 53 such that they would grind or abrade away the crown to expose the embryo.

An example of such a device is any of a variety of rotary tools from Dremel™, 4915 21$^{st}$ Street, Racine, Wis. 53406 USA. Such tools, and similar tools, are commercially available with a variety of working ends such as polishing brushes that have nylon, stainless steel, or carbon steel bristles, if they do not destroy the embryo or a substantial number of the embryo cells.

Tool 300 might be used with the same bristles 306 (or different bristles) to brush, grab, or perturb the embryos to cause them to separate and loosen from the remaining kernel portion 54B so that they either fall out or could be collected for use in another way.

Alternatively, a stationary bench mounted tool 300 could be used and the ear 50 brought by the user against bristles 306.

Through empirical testing, the nature of bristles 306 and the speed of rotation of wheel 304 could be resolved to perform the embryo exposure and embryo extraction functions.

The brushes could be used to remove external tissue or just to scarify, weaken, or create a point of failure but not extract or influence out the internal structure or tissue of the kernels. For example, the brushes could be used in a pre-extraction process where the internal tissue (e.g., the endosperm) is weakened or softened by contact and applying pressure or force to the kernels on the ear without rupturing the pericarp and/or seed coat. Another method could be used to do this. For example, the ear could be subjected to an acceleration field to eject the embryos (as with Embodiments 1-3). Alternatively, grinding discs or drills might be used. On a larger scale, grinding tools are available from a variety of commercial sources. Tool 300 could be manipulated manually so that bristles 306 are in the orientation of FIG. 19 relative to kernels along ear 50. The user would use care to abrade away just enough external tissue from the kernels to expose the embryos, similar to cutting off the crown.

The nature and characteristics of the bristles would have to be appropriately selected according to the desired function. For example, if the brush is used only for accessing the interior of the seed, the bristles or other material for the brush or rotating wheel could be more aggressive than if they are also used to comb the interior of the seed. Optionally, different rotating tool heads might be used for accessing the interior and then extracting the interior material. The extracted embryos may then be moved into contact with a doubling agent and cultured in the agent for providing a doubled haploid embryo for producing doubled haploid plants, such as where the doubled haploids are transferred to a germination media for growing a doubled haploid plant.

Exemplary Embodiment 5

Another approach would include utilizing a fine puncturing tool mounted on a roller device which would rapidly score each seed with a small puncture. Various methodologies could be used, e.g., roller devices, focused air blasts and osmotic pressure, to eject the embryo from the forming seed. An advantage to this process would be the absence of a physical tool inserted into the seed for removal.

FIGS. 20A-C illustrate one such alternative embodiment. A roller 404 would be driven or rotate around axle 402 which could be connected to a motor. Alternatively the operator might manually roll it along an ear of maize which would not be necessarily processed (it could simply be an original ear of FIG. 5 without the crowns removed). On the exterior of roller 404 could be blades or punches 406 that would be aligned with each vertical row of kernels 54. As illustrated in FIG. 20C, each punch 406 would be adapted to penetrate the pericarp of a kernel 54 and expose the embryo 58. The embryos could then be accessed or extracted. The rollers could also be used in a pre-extraction process where the rollers are rolled up and down or around the ear to apply pressure or force to the kernels to soften or weaken the endosperm or other internal tissue to aid in embryo extraction.

An example of the type of punches or blades can be found in commercially available slitting or cutting wheels (e.g., a perforating wheel from Meaden Precision Machined Products Co., 16W210 83rd Street, Burr Ridge, Ill. 60521 USA). Such perforating wheels can be specified to have a certain diameter with a certain number of teeth to perform a certain number of punches or cuts per inch of rotation, as well as the spacing between cuts. They are typically used to create equally spaced perforations when the wheel is rolled across paper, but could be adapted to scoring or penetrating the kernel pericarp to expose the embryo. Several of these perforating wheels could be mounted along a common axle to allow more than one longitudinal row of kernels to be scored or opened at each pass. The axle could be curved to match the curvature of an ear of corn. There could be a depth or similar gauge (like a depth gauge wheel) which could control depth of penetration into the kernels or seed.

The tool could be moved longitudinally along the ear. Or it could be moved transversely around the exterior of the ear perpendicular to the longitudinal axis. Alternatively, the tool could be held fixed and the ear rotated (similar to FIG. 11). Or, both ear and tool could move relative to each other.

Alternatively, a row of punches could be mounted along a bar or cylinder and spaced apart to generally match the spacing between kernels on a maize ear. The bar could be brought into alignment with a longitudinal row of kernels on the ear and manually pushed to remove a portion of the seed coating and expose the embryos in the row, or the cylinder placed parallel to the longitudinal axis of the ear and rolled around the perimeter of the ear (perpendicular to what is shown in FIG. 20A).

One extraction method would be to use an air jet device 410 that would have a nozzle 412 to focus an air jet 414 into each seed 54 to perturb, loosen, and eject the embryo. Empirical testing could be used to select the air jet and its nature and characteristics (e.g., nozzle type, air pressure, etc.) to achieve those functions. An example of an air jet is disclosed in published application US2005/0254053 entitled "Non-destructive single seed or several seeds NIR analyzer and method", assigned to the owner of the present application and incorporated by reference herein.

The tool could simply be used to weaken or damage the seed coat. Once exposed, the embryos could be extracted by hand or by one of the methods previously described. For example, the puncturing could create a point of damage or weakness to the seed coat, the ear could be rotated as with Embodiment 1, 2, or 3, and the internal material ejected and collected. Some other force could be used to eject the internal tissue. Non-limiting examples include osmotic pressure, air blasts, or water jets.

The force of slitting or punching is accomplished by either manually pressing the slitting or punching tool against the ear of maize or vise versa. It is also possible that a mechanized slitting or punching machine could be configured to accomplish the functions of exposing the embryos of a plurality of kernels on the ear.

Exemplary Embodiment 6

Another approach for rapid seed coat removal might include the use of etching lasers or galvo scanning lasers to rapidly remove seed coat tissue without burning other seed structures.

Figure 21:
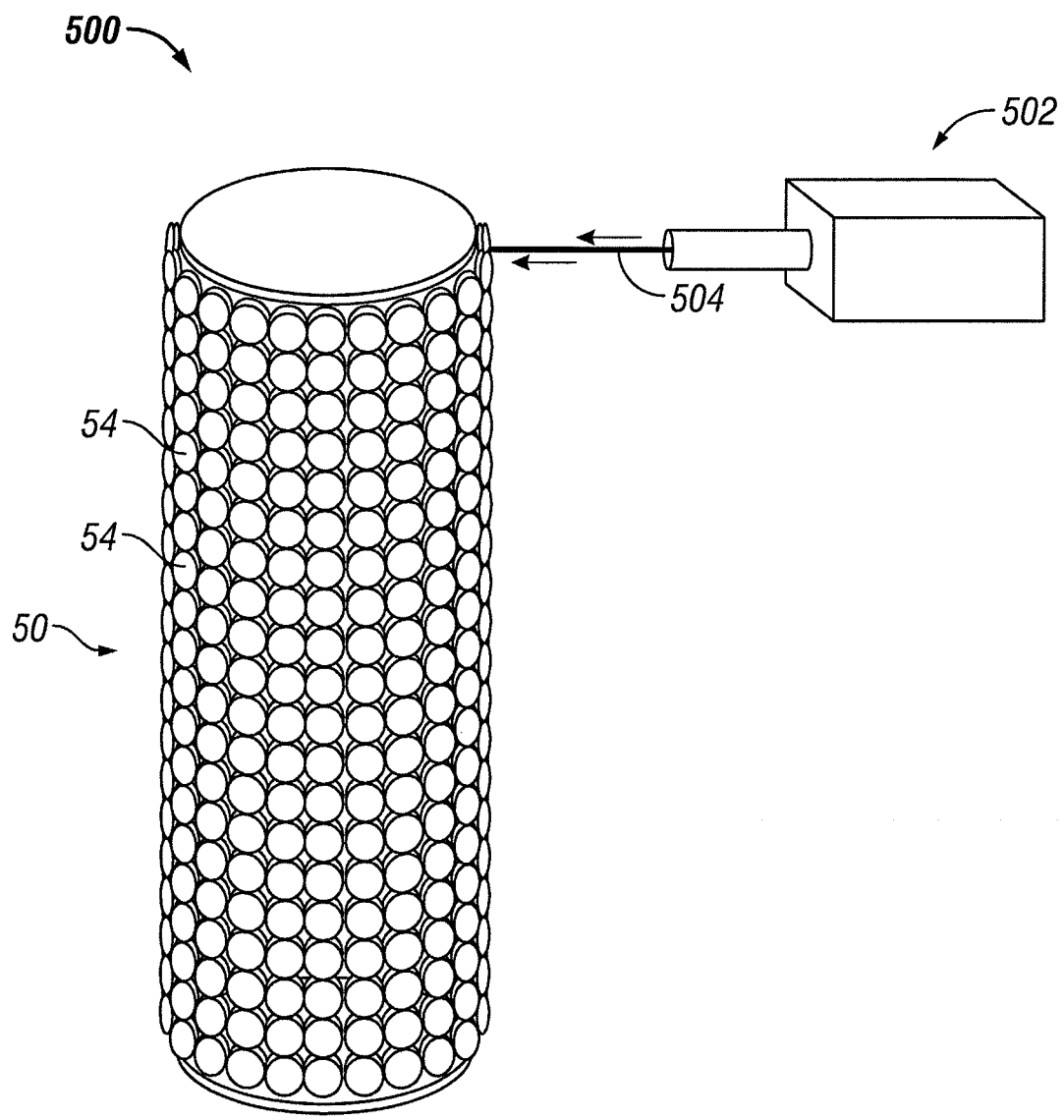
FIG. 21 is a diagrammatic view of a still further embodiment of the present invention using a laser beam to cut off the crown of kernels or to etch or ablate the exterior to gain access to the interior.

FIG. 21 illustrates such type of force to expose an embryo. A laser device 502 could focus a laser beam 504 on each kernel 54 to cut or ablate the seed coat and endosperm to expose the embryo. This could be used to process an ear 50 to a form akin to that of FIG. 8.

An example of laser ablation or etching is set forth in Provisional Application Ser. No. 61/092,863, filed Aug. 29, 2008, which application is assigned to the owner of the present application and incorporated by reference herein in its entirety. It describes use of a $CO_2$ laser to remove pericarp tissue. (e.g., a Firestar™ f201 Series, Model # FSF201SB, water-cooled sealed carbon dioxide ($CO_2$), 200 watt laser commercially available from Synrad, Inc. of Mukiteo, Wash. USA). Other types of gas lasers could be used, as can other types of lasers (e.g., chemical, metal vapor, solid state (e.g., YAG) and semiconductor). Any of the typical types of laser cutting systems could be used, including but not limited to flying optics, hybrid, and pivot-beam. The laser normally would include an optics package to focus and control the laser beam systems. An example of an optic system is a Haas Laser Technologies Inc. 1.25" series beam delivery system with a 5" focal lens. By empirical testing and calibration, laser 502 can be set to ablate a pattern or area of one side of a seed to a relatively controllable depth. Following the manufacturer's set up instructions, laser 502 can be configured to produce laser beam 504 of a certain width, power, modulation, and color designed for desired ablation of a surface of a corn kernel to remove an area of seed coat and provide access to tissues (e.g., embryo) underneath the seed coat, and to do so non-destructively. It is to be understood that it may be possible that other forms of energy or forces could be used for the removal of tissue or structure from seed. There are a variety of automated positioning systems available with lasers to control movement of the laser from kernel to kernel, and row to row around the ear. The laser and/or the ear can be moved relative to one another.

Thus, light energy is the force used to remove external kernel tissue and expose internal kernel tissue. The energy would be controlled so as to gain access to the embryo or targeted internal tissue or structure non-destructively. The light energy can be controlled to ablate, etch, or cut a maize seed, including seed coat, without burning or destroying the embryo.

Use of laser avoids any touching or handling of the seed and could lower contamination risks.

Once the embryos have been exposed, the ear could be shaken or spun to eject the embryos. Alternatively, an air jet or other force could be used to eject the embryos. Flushing with liquid or air, or osmotic pressure, are a few other possibilities.

A laser could also be used to simply cut off the crowns of each kernel by either moving each kernel through the beam or vise versa. An example of crown removal with a laser is disclosed in Provisional Application Ser. No. 61/092,863, filed Aug. 29, 2008, which application is assigned to the owner of the present application and incorporated by reference herein in its entirety.

Exemplary Embodiment 7

Figure 22A:
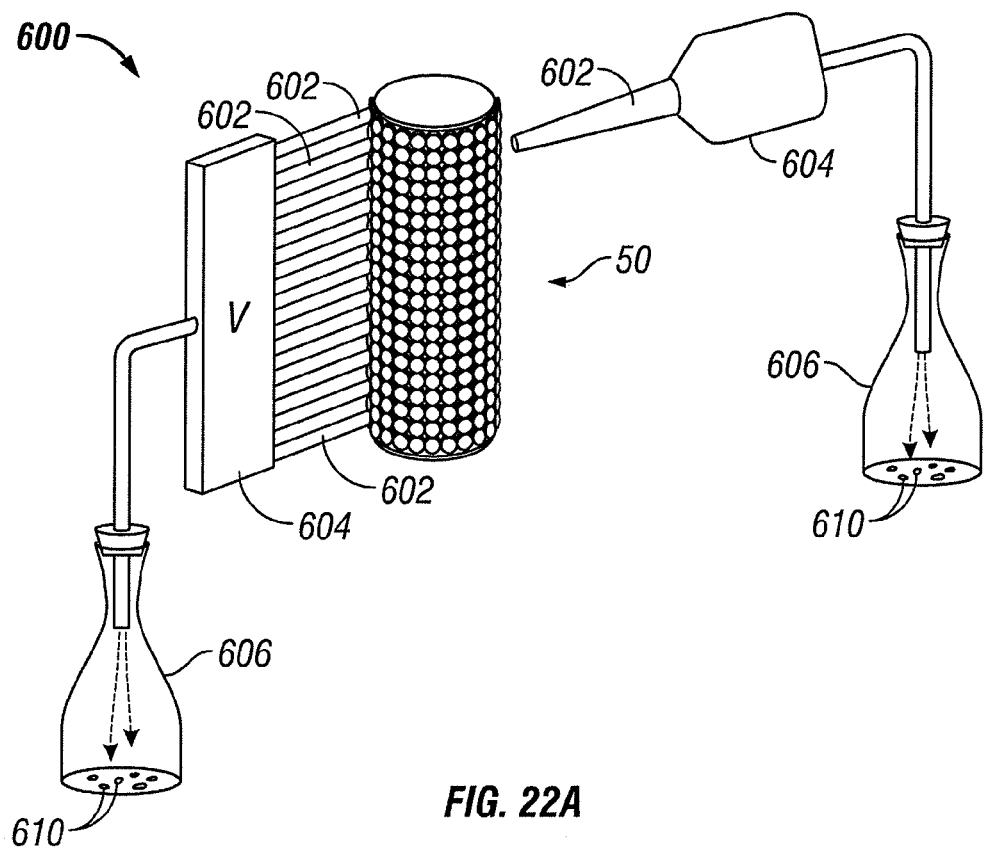
FIG. 22A is a diagrammatic view of another exemplary embodiment according to the present invention, where exposed internal tissue of structure of maize kernels on an ear can be extracted with a vacuum tool.
Figure 22B:
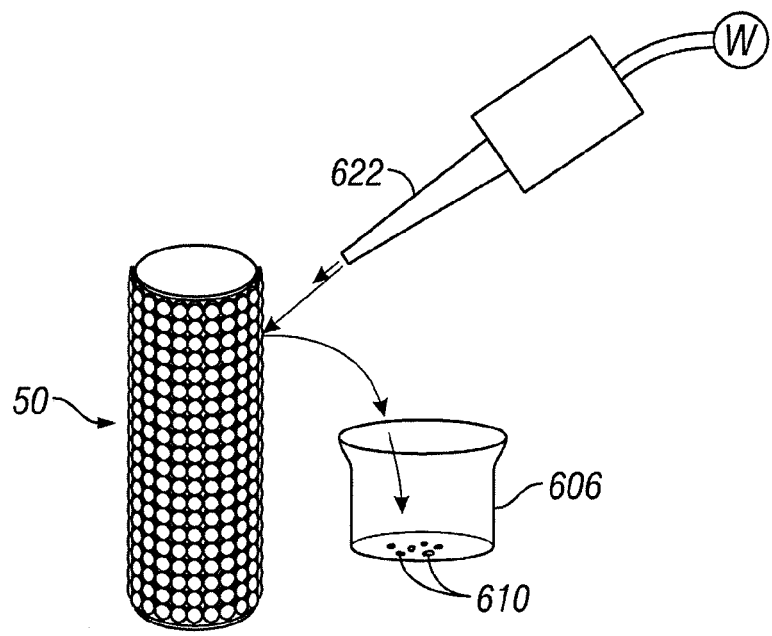
FIG. 22B is a diagrammatic view of another exemplary embodiment according to the present invention, where exposed internal tissue or structure of maize kernels on an ear can be extracted, forced out, or washed out with a pressurized liquid stream or jet tool.

FIGS. 22A and 22B show further embodiments for extracting internal seed tissue or structure. In each case the ear is pre-processed to create an ear 50 with internal tissue exposed (e.g., one option is shown in FIGS. 5-8).

In FIG. 22A, system 600 uses a commercially available disposable vacuum pick 604 (with a disposable vacuum pipette 602) which has a diameter to pull by vacuum the embryo (and perhaps other internal content) 610 of each seed into a container 606. It would work similarly to a medical suction device to remove the embryo, and perhaps some endosperm, from the exposed interior of the seed. Internal tissue such as the endosperm may be softened or weakened (e.g., the binding link between the embryo and endosperm weakened or softened) to promote easier embryo extraction. The vacuum pick can be like a dental suction tool. It can use vacuum through a relatively small diameter tube that can be inserted into an exposed kernel to suction out the embryo and perhaps some endosperm directly into a container.

An alternative would be a vacuum wand, such as commercially available from Advanced Vacuum Technology, a division of Fluoro Mechanic Co., Ltd. 7-21-1, Hirai Edogawa-ku Tokyo 132-0035, Japan. It could act like tweezers to pick out the embryo and allow the operator to move it over to a container.

Variable diameter picks 604 are commercially available. The diameter can be selected through empirical testing. For example, one size might be used to extract maize embryos. Another might be used to extract other internal tissue or structure or to extract both the embryo and other tissue or structure (e.g., the embryo and endosperm).

The vacuum could pull the embryo (and perhaps other material) into a flask or other container. The targeted material (e.g., embryos) could be filtered or sorted out and isolated. This could be in fluid.

FIG. 22A shows an option. A plurality of pipettes 602 could be spaced apart the distance between kernels along a row on ear 50 to create a type of vacuum "comb". It could be operated to simultaneously pull embryos from an entire row (or portion of a row) of ear 50. It would simply be moved row-to-row and collect internal tissue into container 606. Alternatively, the ear could be rotated (e.g., one example is shown in FIGS. 2 and 12).

FIG. 22B illustrates a similar principle except instead of vacuum, pipette 622 directs pressurized water (e.g., water from a Water Pik™ water jet available from Water Pik, Inc. of Fort Collins, Colo. USA) to the location of an exposed kernel to knock or flush the internal tissue, including embryo, into container 606 (e.g., a beaker). It would simply be moved from kernel to kernel to collect embryos.

Exemplary Embodiment 8

An alternative method extraction is the use of osmotic force to cause a seed to swell, the seed coat to break or burst, and the internal contents to expel or be available for collection.

Osmosis is the spontaneous net movement of water across a semipermeable membrane from a region of high solute concentration to a solution with a low solute concentration, and down a solute concentration gradient. It is a physical process in which a solvent moves, without input of energy, across a semi permeable membrane (permeable to the solvent, but not the solute) separating two solutions of different concentrations. Osmosis releases energy, and can be made to do work, as when a growing tree-root splits a stone. In biology, hypotonic solutions contain a low concentration of solute relative to another solution (e.g., the cytoplasm of a cell). Given a cell placed in a hypotonic environment (e.g., a hypotonic solution), osmosis causes a net flow of water into the cell, causing the cell to swell and possibly burst. In an analogous manner, a fluid such as water could be controlled through the permeable seed coat of a seed to swell the seed, and thus the seed coat, until the seed coat bursts. The interior of the seed would then be exposed or more accessible. Pre-extraction procedures such as rolling the ear on a hard surface without rupturing the pericarp for softening or weakening the endosperm may also be employed so as to increase embryo extraction rates.

Exemplary Embodiment 9

Figure 23:
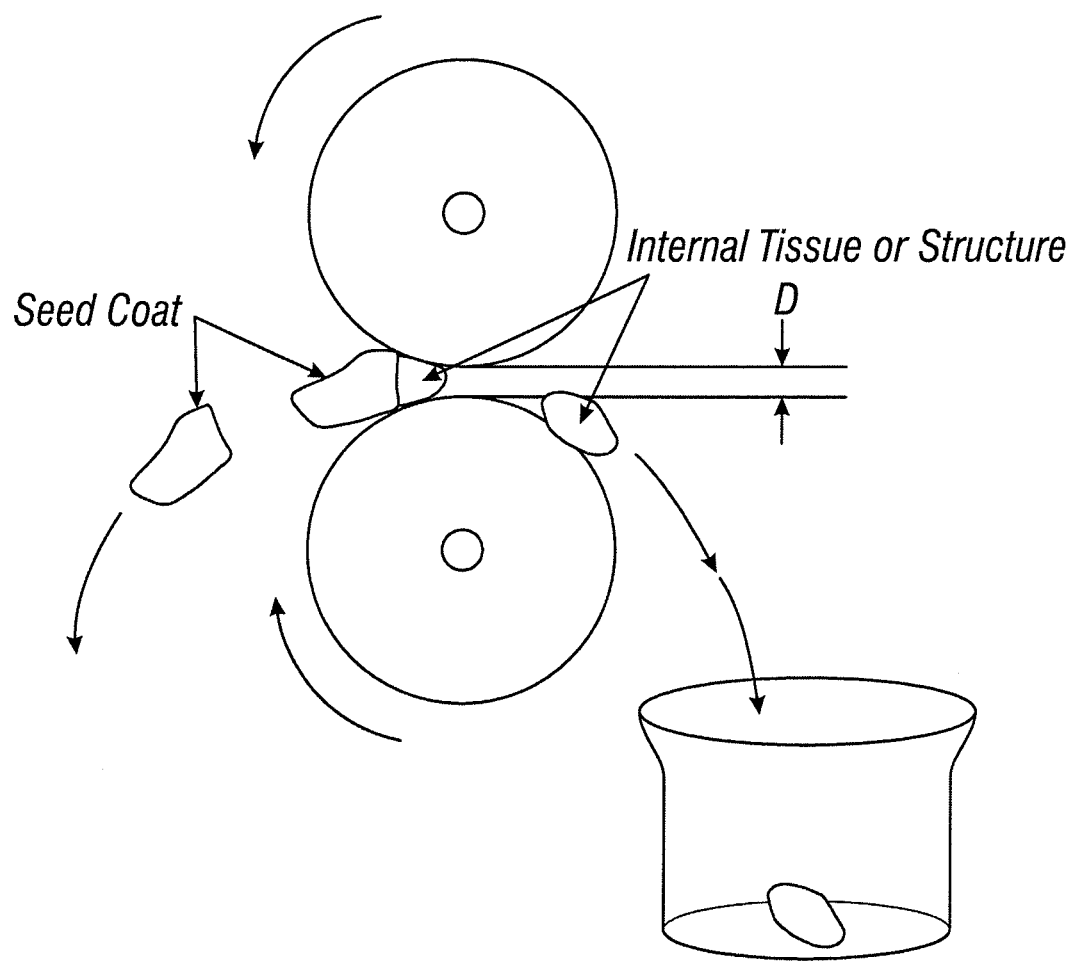
FIG. 23 is a diagrammatic depiction of use of spaced-apart, oppositely turning rollers through which seed can be passed to remove the seed coat and/or force internal tissue out of the external tissue or seed coating.

Some seed can be processed by using pressure against the seed to burst or open the seed, and spill its internal contents, or at least expose it to easy collection. FIG. 23 illustrates diagrammatically such a system. Oppositely rotating rollers are spaced a distance D that is less than the thickness of the seed. The seed is introduced and the pressure removes the seed coat and spills the internal contents into a collection container. The seed could be pre-processed by puncture to help the internal contents to spill. This same process could be used as a pre-extraction procedure where the rollers are separated a sufficient distance and rotated in the same direction to apply pressure to each kernel sufficient to soften or weaken the endosperm but not rupture the pericarp and/or seed coat to help aid in the separation of the embryo from the kernel.

This method could be applied to, for example, soybean seed or guar seed.

Summary

It can be appreciated that a number of different forms can be taken to either access the embryo or extract the embryos suitable for use in the process of doubled haploid plant production. A multitude of mechanical and electronic designs can be envisioned, as can the methods of deploying these. Some examples have been set forth above.

An additional example for cutting open a seed is a jet of water. Water jet cutters are capable of slicing into substances as hard as metal by using a jet of water at high velocity and pressure (e.g., thirty to sixty thousand PSI), or a mixture of water and an abrasive substance. It is similar to water erosion but accelerated and concentrated by orders of magnitude. Machines are commercially available from a variety of sources. One example is International Waterjet Machines, 1108 W. Valley Blvd, Ste 6-292, Alhambra, Calif. 91803, USA.

Another option would be to use a water stream to capture the embryos or a cushion of some shock absorbing material to avoid damaging the cells. For example, after the embryos are collected, they could be separated from the cellular debris by a brief centrifugation on a higher density liquid cushion (e.g., sucrose or polyethylene glycol cushion). Extraction of intact immature embryos is also further facilitated by conducting some pre-extraction process on the kernels to help weaken the bonds between the embryo and internal seed tissue, such as the endosperm, without rupturing the pericarp and/or seed coat. One approach to development of such devices is to modify existing commercial or proprietary devices to add the capability to capture and clean the embryos. Additional ideas to facilitate rapid isolation of embryos for downstream processes are possible.

Figure 24:
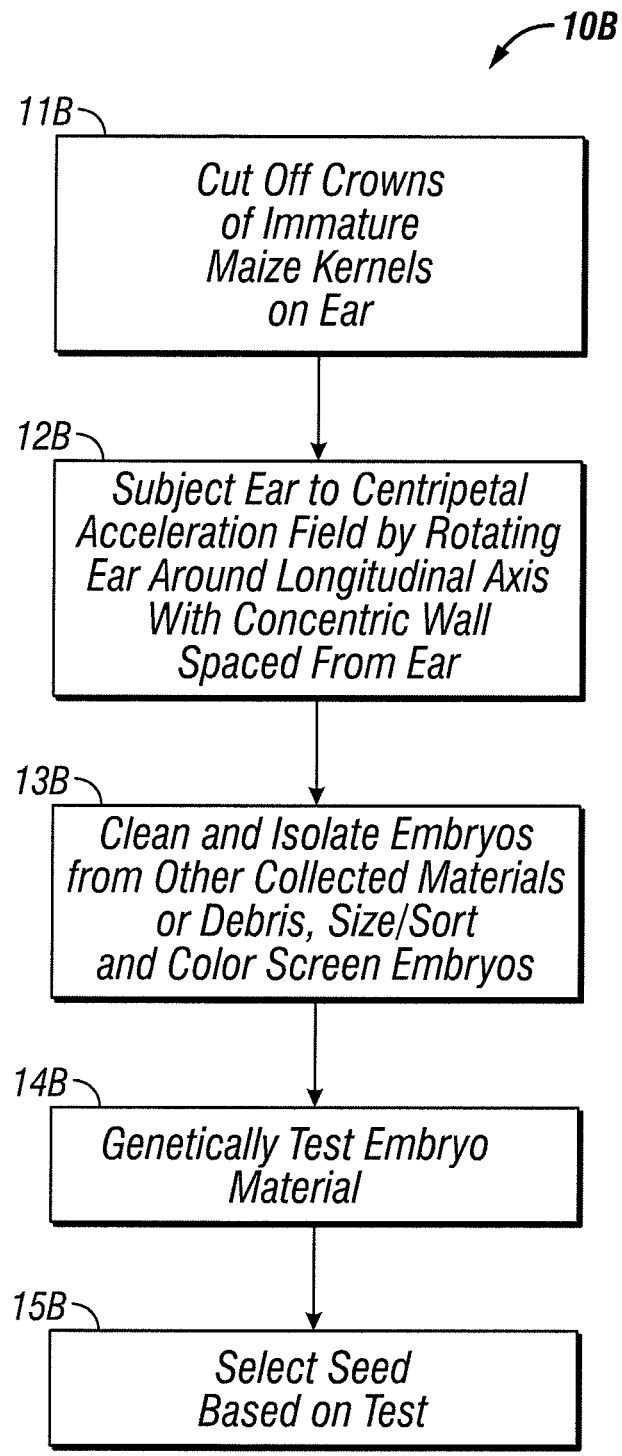
FIG. 24 is a flow diagram of a method of extracting maize embryos according to the certain embodiments of the invention.

FIG. 24 sets forth a flow diagram of a method 10B of extracting embryos from maize kernels. It follows the general method of FIG. 1. In this example, access to the embryos is gained by cutting the crowns of the kernels off while attached to the ear without damaging the embryos (step 11B). An optional pre-extraction process where the ear is subjected to pressure or force by rolling on a flat surface to loosen or weaken bonds between the embryo and endosperm to aid in embryo extraction may be used prior to cutting the crowns of the kernels off. The ear is then subjected to an acceleration field (step 12B) sufficient to eject the embryos, and some other internal tissues and structures, from the ear into a surrounding container. The embryos are then isolated from other materials (step 13B). If desired, the isolated embryos can be sorted or sized and then used (step 13B). The embryo material is then tested (step 14B). Based on step 14B, seeds are selected (step 15B). Analogous methods to that of FIG. 24 can be used for extracting other internal tissue or structure of maize seed or other species of plant.

Experimental Results

The inventors have conducted experiments to test various embodiments of the present invention. One such experiment comprised two treatments: a control treatment, in which embryos were manually extracted, and a test treatment, in which embryos were mechanically extracted via a centrifugal embryo extractor similar to Exemplary Embodiment 2. Nine genotypes were evaluated using five ears of maize per genotype per treatment. Data was collected regarding germination, contamination and callus formation of haploids. Observations were also gathered regarding marker expression and growth.

For the test treatment, a hole was drilled in the cob of each of the test treatment maize ears. The ears were then rolled on a hard surface without breaking the pericarp. Next, the caps of the kernels were cut off (e.g., approximately the top third of the kernels were removed). Each ear was then inserted into the centrifugal embryo extractor and was rotated at approximately 9,000 RPM. For each ear, the extracted embryos and the endosperm were transferred to a clean paper plate by rinsing the cylinder of the centrifugal embryo extractor with sterile water having 15% sucrose concentration (weight/volume). The embryos were then removed from the paper plate and transferred to doubling media. Next, the embryos were cultured overnight and the haploid embryos were transferred to germination media. The haploids were then grown for 5-7 days, at which point contamination and germination rates were evaluated.

For the control treatment, embryos were extracted manually, using prior art techniques.

Germination, contamination, and callus formation data was analyzed using two sample t-tests and confidence intervals. The inventors found no significant difference in percentage of haploid germination between the embryos that had been mechanically extracted and the embryos that had been manually extracted (mean percentage of germination for embryos that had been mechanically extracted was approximately 79.7%; mean percentage of germination for embryos that had been manually extracted was approximately 83.5%). The inventors also found no significant difference in the percentage of haploids with callus formation (mean percentage of haploids having callus formation for embryos that had been mechanically extracted was approximately 17.1%; mean percentage of haploids having callus formation for embryos that had been manually extracted was approximately 12.5%). In addition, the inventors found no significant difference in the percentage of haploid contamination (mean percentage of embryos contaminated that had been mechanically extracted was approximately 4.0%; mean percentage of embryos contaminated that had been manually extracted was approximately 2.05%).

The inventors found weaker marker expression in genotypes for embryos washed with sterile distilled water after mechanical extraction. No difference of marker expression was found between the embryos that had been mechanically extracted and the embryos that had been manually extracted. The inventors found a significantly higher percentage of haploid embryos per ear for the ears that were subjected to manual embryo extraction as compared to the ears that were subjected to mechanical embryo extraction (mean percentage of haploid embryos per ear for ears subjected to manual extraction was approximately 11.65%; mean percentage of haploids per ear for those ears that were subjected to mechanical extraction was approximately 7.58%). The inventors hypothesized that this result was likely because those ears that were subjected to mechanical extraction were shortened on both ends in order to be received by the centrifugal embryo extractor, thus resulting in less overall kernels available for extraction.

Another similar experiment was conducted in which a control treatment comprised embryos that were manually extracted and a test treatment comprised embryos that were mechanically extracted. Ten genotypes were evaluated. Data was collected regarding percentage callus formation of haploids, percentage germination, percentage of double haploid embryos transplanted, percentage of survival in the field two weeks after transplanting, percentage survival in the field at flowering, percentage of plants pollinated, and percentage of double haploids with more than 25 kernels per ear.

The embryos of the test treatment were extracted using a centrifugal embryo extractor in a similar manner as that described above. The embryos of the control treatment were extracted manually, using prior art techniques.

The inventors found that there were significant differences in callus formation (mean percentage of haploids with callus for embryos that had been mechanically extracted was approximately 16.3%; mean percentage of haploids with callus for embryos that had been manually extracted was approximately 9.7%). The inventors hypothesized that this may be due to physical damage that may have occurred during extraction or cell damage caused by yeast contamination. The inventors found that there was a significantly higher percentage of germination for the control test treatment (mean percentage of germination for embryos that had been mechanically extracted was approximately 78.3%; mean percentage of germination for embryos that had been manually extracted was approximately 88.3%). The inventors hypothesized that this was due to contamination and associated callus formation. The inventors found no significant differences in the percentage of double haploid embryos transplanted (mean percentage of double haploid embryos transplanted that were mechanically extracted was approximately 86.7%; mean percentage of double haploid embryos transplanted that were manually extracted was approximately 89.3%). The inventors found no significant differences in the percentage of survival in the field two weeks after transplanting the double haploid seedlings into the ground (mean percentage survival for plants derived from embryos that had been mechanically extracted was approximately 87.2%; mean percentage of survival for plants derived from embryos that had been manually extracted was approximately 88.6%). The inventors also found no significant differences in survival in the field at flowering (mean percentage survival at flowering for plants derived from embryos that had been mechanically extracted was approximately 96.92%; mean percentage survival at flowering for plants derived from embryos that had been manually extracted was approximately 97.76%). The inventors found no significant differences in the production of fertile flowers (mean percentage of pollinated plants derived from embryos that had been mechanically extracted was approximately 84.0%; mean percentage of pollinated plants derived from embryos that had been manually extracted was approximately 85.6%). In addition, the inventors found no significant differences in the percentage of plants having more than 25 kernels per ear (mean percentage of plants having more than 25 kernels per ear derived from embryos that had been mechanically extracted was approximately 62.2%; mean percentage of plants having more than 25 kernels per ear derived from embryos that had been manually extracted was approximately 66.3%).

Applications

As is well appreciated by those skilled in the art, the uses of an embryo extracted from a seed are many and varied. As discussed earlier, one use would be to evaluate the embryo tissue or cells chemically, physically, or genetically. Another use would be to use extracted embryos for doubled haploid plant production as discussed previously. Such analysis can be useful in research and development regarding the seed or the plant.

Discussion of use of analysis of specific tissue of a seed is described in Provisional Application Ser. No. 61/092,863, filed Aug. 29, 2008, which application is assigned to the owner of the present application and incorporated by reference herein in its entirety. Examples include the following.

A number of analyses can be applied to the seed after tissue has been removed. One example is genetic testing. By methods known in the art, access or exposure of the embryo, for example, allows for a wide variety of assays including gene expression (e.g. micro array), genome analysis (e.g. QTL analysis, SNP analysis, RFLP analysis), and protein analysis (e.g. immunohistochemistry).

In one example, the mRNA level of a gene of interest can be quantified through the use of real-time polymerase chain reaction (PCR). In real-time PCR, the seed with the exposed embryo is prepared and immersed in a PCR mixture and PCR amplifications are performed. A detector interrogates the resultant solution and can generate a signal representative of quantity of mRNA present for the gene of interest. A variety of PCR detectors are commercially available. One example is an optical detector for PCR (e.g. Chromo4™ Real-Time PCR Detector from Bio-Rad Laboratories, Inc., Life Science Research Group, 2000 Alfred Nobel Drive, Hercules, Calif. 94547 USA).

Another analysis could be cellular level analysis. An example with respect to corn is described at Consonni et al., Annals of Botany 2005 96(3):353-362, which is incorporated by reference herein.

A still further example is nanoscale analysis. See, e.g., Borner et al., Plant Physiol. 2005 January; 137(1): 104-116, incorporated by reference herein.

Other procedures or analyses are, of course, possible. Chemical analysis of the seed can be performed. The tissue separation provides a sample for such analyses. One skilled in the art is familiar with the different analysis and testing that can be done on seed.

Once analysis has been completed, the information of the analysis can be used to, for example, distinguish a seed from other seed. This can be used to select one seed over another for use in plant breeding programs. One example is a seed that, through genotyping, is indicated to be more drought-resistant than other genotypes. By effective non-destructive exposure and/or extraction of an embryo, and by an appropriate genotyping assay, a seed indicative of drought resistance genetic make-up can be identified.

Importantly, non-destructive tissue removal and analysis allows such identification to be made without either planting the seed and waiting to test a tissue sample from its growing plant or having to use the land or greenhouse space, labor, and supplies to plant and grow the seed into plants. As can be appreciated, this represents a potential substantial savings in time, labor, and resources, including land resources, for selection processes for seed companies.

An important reason to expose interior tissues of a corn seed is to gain access to male and female genetic material to assay and evaluate genetic content. This allows researchers the ability to know if a seed contains a gene of interest. If so, the seed is then identified as a candidate for further research or commercialization. The methods herein use controlled forces to remove specific seed tissue in a non-destructive manner. This, in turn, allows testing and analysis, seed selection, and then planting and germination of the selected seed for further use. One further use is development of commercial quantities of seed from the selected seed; such as a commercial seed product for seed companies.

There are other beneficial applications for a methodology of processing seed to remove a certain relatively accurate amount of tissue from the seed. A variety of situations exist where removal of some portion of the seed is desired. The method described above utilizes steps to non-destructively remove desired seed tissues. For example, embryo material or cells can be used to produce a plant (such as a doubled haploid plant or embryo) or plantlet, a plurality of plants, a crossed-plant, callus material, or a mass of embryonic material to obtain a purified protein. Other uses for seed tissue or exposed seed tissue are well known in the art.

Other variations or alternatives are possible and recognized by those skilled in the art, and are intended to be within the scope of this invention.

Automation, the relatively high volume or rapid handling of ears and recovering of embryos is facilitated by many of the above-described embodiments. The use of acceleration is one way. Acceleration can be quenched to avoid damage to the embryos.

Those skilled in the art will appreciate that aspects of these embodiments can be applied to either batch processing of seed or to individual seed. For example, individual seed could have a portion of its external tissue or structure removed individually by a number of the methods and apparatus described earlier. Provisional Application Ser. No. 61/092, 863, filed Aug. 29, 2008, which application is assigned to the owner of the present application and incorporated by reference herein in its entirety, illustrates one way to singulate seed and then cut off the crowns one by one. Extraction of internal structure one seed at a time is also an option. Several examples have been described. In these cases, throughput may be reduced, but can still be high throughput compared to the state of the art methods described in the Background of the Invention.

As indicated elsewhere, many if not most of the steps of these methods can be mechanized and/or at least substantially automated. This could include handling of maize ears or other seed on its vegetative carrier. It could include post-processing steps, including testing, evaluation, and storage or recording of the results of the same.

What is claimed is:

1. A method for extracting an embryo from enclosing tissue or structure for one or more seed in at least a semi-automated fashion comprising:
   a. exposing internal tissue or structure of each seed by disrupting or damaging enclosing tissue or structure; and
   b. removing the embryo from the enclosing tissue or structure;
   c. wherein at least one of steps of exposing and removing are accomplished with mechanical or non-manual forces non-destructive to the embryo;
   d. wherein the step of exposing comprises removing one half of each seed; and
   e. wherein the step of removing comprises subjecting each seed to centripetal acceleration.

2. The method of claim 1 wherein the step of exposing internal tissue or structure further comprises at least one of:
   a. manual cutting;
   b. cutting with a machine;
   c. cutting with a laser beam;
   d. ablating;
   e. grinding;
   f. puncturing;
   g. squeezing; and
   h. loosening.

3. The method of claim 1 wherein the embryo is suitable for use in doubled haploid plant production.

4. A method for extracting an embryo from enclosing tissue or structure of a batch of seed in at least a semi-automated fashion comprising:
   a. exposing internal tissue or structure of each seed of the batch of seed by disrupting or damaging enclosing tissue or structure; and
   b. approximately concurrently removing the embryo from the enclosing tissue or structure of each seed of the batch of seed;

c. wherein at least one of steps of exposing and removing are accomplished with mechanical or non-manual forces which are non-destructive to the embryo;

d. wherein the step of exposing comprises removing one half of each seed; and e. wherein the step of removing comprises subjecting each seed to centripetal acceleration.

5. The method of claim 4 wherein the embryo comprises genetic information about the seed and the enclosing tissue or structure comprises a seed coat.

6. The method of claim 4 further comprising collecting and isolating the embryo.

7. An apparatus for extracting an embryo from one or more seed comprising:
   a. means for exposing internal tissue or structure of each seed by removing, disrupting, or weakening at least some enclosing tissue or structure of the seed; and
   b. means for removing the embryo from the enclosing tissue or structure of the seed by non-manual forces in at least a semi-automated fashion to remove or disrupt internal tissue or structure holding the embryo in or to the seed;
   c. wherein the means for exposing is configured to remove one half of each seed; and
   d. wherein the means for removing the embryo comprises a device adapted to produce centripetal acceleration or deceleration.

8. The apparatus of claim 7 wherein the means for exposing specific internal tissue or structure further comprises at least one of:
   a. a manually-operable cutter;
   b. a machine controlled cutter;
   c. a laser beam cutting device;
   d. a laser beam ablating device;
   e. a grinder;
   f. an abrader;
   g. a puncture tool;
   h. a means to apply mechanical pressure to a seed;
   i. a means to apply internal pressure to a seed;
   j. a means to peel external tissue or structure; or
   k. a means for loosening external tissue or structure.

9. The apparatus of claim 7 further comprising a collection vessel for the removed internal tissue or structure.

10. The apparatus of claim 7 further comprising a means to hold a plurality of seed for high throughput batch processing of the plurality of seed.

11. The apparatus of claim 7 further comprising a means to apply pressure on the seed before exposing and removing targeted internal tissue or structure to loosen or weaken bonding between the targeted internal tissue or structure and the enclosing tissue or structure so as to improve extraction of the targeted internal tissue or structure from the enclosing tissue or structure.

* * * * *